(12) United States Patent
Cha et al.

(10) Patent No.: US 12,091,679 B2
(45) Date of Patent: Sep. 17, 2024

(54) STORAGE METHOD AND BANKING SYSTEM OF NT CELL

(71) Applicants: SUNGKWANG MEDICAL FOUNDATION, Seoul (KR); CHA BIOTECH CO., LTD., Seoul (KR)

(72) Inventors: Kwang Yul Cha, Seongnam-si (KR); Dong Ryul Lee, Seoul (KR); Young Gie Chung, Shrewsbury, MA (US); Jihwan Song, Seoul (KR); Jin Hee Eum, Seoul (KR)

(73) Assignees: SUNGKWANG MEDICAL FOUNDATION, Seoul (KR); CHA BIOTECH CO., LTD., Seoul (KR)

( * ) Notice: Subject to any disclaimer, the term of this patent is extended or adjusted under 35 U.S.C. 154(b) by 436 days.

(21) Appl. No.: 15/745,301

(22) PCT Filed: Jul. 18, 2016

(86) PCT No.: PCT/KR2016/007795
§ 371 (c)(1),
(2) Date: Jan. 16, 2018

(87) PCT Pub. No.: WO2017/014513
PCT Pub. Date: Jan. 26, 2017

(65) Prior Publication Data
US 2018/0208891 A1 Jul. 26, 2018

(30) Foreign Application Priority Data

Jul. 17, 2015 (KR) .................. 10-2015-0101996
Jul. 18, 2016 (KR) .................. 10-2016-0090711

(51) Int. Cl.
| | | |
|---|---|---|
| *C12N 5/074* | (2010.01) | |
| *C12N 5/00* | (2006.01) | |
| *C12N 5/0775* | (2010.01) | |
| *C12N 5/0793* | (2010.01) | |
| *C12N 5/10* | (2006.01) | |
| *C12N 15/873* | (2010.01) | |

(52) U.S. Cl.
CPC ......... *C12N 5/0607* (2013.01); *C12N 5/0018* (2013.01); *C12N 5/062* (2013.01); *C12N 5/0665* (2013.01); *C12N 5/0696* (2013.01); *C12N 5/10* (2013.01); *C12N 15/873* (2013.01); *C12N 2500/46* (2013.01); *C12N 2506/03* (2013.01); *C12N 2517/04* (2013.01); *C12N 2517/10* (2013.01); *C12N 2760/18821* (2013.01); *C12N 2760/18822* (2013.01); *C12N 2760/18831* (2013.01)

(58) Field of Classification Search
CPC .... C12N 5/0607; C12N 5/0018; C12N 5/062; C12N 5/0665; C12N 5/0696; C12N 5/0666; C12N 5/0668; C12N 2500/46; C12N 2506/03; C12N 2506/1392; C12N 2517/04; C12N 2517/10; C12N 2760/18821; C12N 2760/18822; C12N 2760/18831; A01N 1/0221
See application file for complete search history.

(56) References Cited

U.S. PATENT DOCUMENTS

| | | | |
|---|---|---|---|
| 8,647,872 B2 | 2/2014 | Roh et al. | |
| 2004/0091936 A1* | 5/2004 | West ................. | C12N 15/85 435/7.1 |
| 2007/0243610 A1 | 10/2007 | Roh et al. | |
| 2008/0299091 A1 | 12/2008 | Revazova et al. | |
| 2011/0065192 A1 | 3/2011 | Roh et al. | |
| 2013/0276154 A1 | 10/2013 | West | |
| 2014/0154800 A1 | 6/2014 | Roh et al. | |
| 2014/0234968 A1 | 8/2014 | Chung et al. | |
| 2016/0186133 A1 | 6/2016 | Revazova et al. | |
| 2018/0355043 A1* | 12/2018 | Martinez ............ | A61P 37/02 |

FOREIGN PATENT DOCUMENTS

| | | |
|---|---|---|
| KR | 10-2011-0117288 A | 10/2011 |
| WO | WO 03/100018 A2 A3 | 12/2003 |
| WO | 2008/124142 A1 | 10/2008 |
| WO | WO 2014/125363 A1 | 8/2014 |
| WO | WO-2014144754 A1 * 9/2014 | ........... C12N 5/0606 |

OTHER PUBLICATIONS

Tachibana et al., "Human Embryonic Stem Cells Derived by Somatic Cell Nuclear Transfer", 2013, Cell 153, p. 1228-1238.*
Song et al., "Inactivated Sendai-virus-mediated fusion improves early development of cloned bovine embryos by avoiding endoplasmic-reticulum-stress-associated apoptosis", 2011, Reproduction, Fertility and Development 23, p. 826-836.*
Huh et al., "HLA-A, -B and -DRB1 polymorphism in Koreans defined by sequence-based typing of 4128 cord blood units", 2013, International Journal of Immunogenetics 40, p. 515-523.*
Huh JY, Yi DY, Eo SH, Cho H, Park MH, Kang MS. HLA-A,-B and-DRB 1 polymorphism in K oreans defined by sequence-based typing of 4128 cord blood units. International journal of immunogenetics. Dec. 2013;40(6):515-23; cited in previous Office action and filed in IFW on Jan. 8, 2021. (Year: 2013).*
Reche PA, Reinherz EL. Sequence variability analysis of human class I and class II MHC molecules: functional and structural correlates of amino acid polymorphisms. Journal of molecular biology. Aug. 15, 2003;331(3):623-41. (Year: 2003).*

(Continued)

*Primary Examiner* — Allison M Fox
(74) *Attorney, Agent, or Firm* — Oblon, McClelland, Maier & Neustadt, L.L.P.

(57) ABSTRACT

Provided are a storage method and a banking system of cells prepared using somatic cell nuclear transfer (NT) technology with homozygous genotypes of genes of human leukocyte antigen (HLA)-A, HLA-B, HLA-DR, and the like. The banking of NT cell-derived stem cells may be applied to autologous or allogenic patients and can provide transplantable cells and tissue materials for the treatment of various diseases such as diabetes, osteoarthritis, Parkinson's disease, and the like.

5 Claims, 7 Drawing Sheets

(56) References Cited

OTHER PUBLICATIONS

Yamada M, Johannesson B, Sagi I, Burnett LC, Kort DH, Prosser RW, Paull D, Nestor MW, Freeby M, Greenberg E, Goland RS. Human oocytes reprogram adult somatic nuclei of a type 1 diabetic to diploid pluripotent stem cells. Nature. Jun. 2014;510(7506): 533-6. (Year: 2014).*
Egli, D. and Chia, G., 2014. A protocol for embryonic stem cell derivation by somatic cell nuclear transfer into human oocytes. https://doi.org/10.1038/protex.2014.013; last retrieved Mar. 7, 2022. (Year: 2014).*
Young Gie Chung, et al., "Human Somatic Cell Nuclear Transfer Using Adult Cells," Cell Stem Cell, vol. 14, No. 6, Jun. 5, 2014, 19 pages.
International Search Report issued Oct. 25, 2016 in PCT/KR2016/007795 filed Jul. 18, 2016.
Extended European Search Report issued Dec. 6, 2018 in corresponding European Patent Application No. 16828017.0, 8 pages.
Office Action issued Jan. 8, 2019 in corresponding Japanese Patent Application No. 2018-521814, 4 pages.
Paul A.C. Cloos, et al., Erasing the methyl mark: histone demethylases at the center of cellular differentiation and disease, Genes & Development 22:1115-1140 © 2008, by Cold Spring Harbor Laboratory Press ISSN 0890-9369/08; www.genesdev.org.
Jingjing Li, et al., A Novel Histone H4 Arginine 3 Methylation-sensitive Histone H4 Binding Activity and Transcriptional Regulatory Function for Signal Recognition Particle Subunits SRP68 and SRP72, the Journal of Biological Chemistry vol. 287, No. 48, pp. 40641-40651, Nov. 23, 2012 © 2012 by The American Society for Biochemistry and Molecular Biology, Inc. Published in the U.S.A.
Roselyne M Labbé, et al., Histone lysine demethylase (KDM) subfamily 4: structures, functions and therapeutic potential, Am J Transl Res 2014;6(1):1-15, www.ajtr.org /ISSN:1943-8141/ AJTR1311006.
Ngai Cheung, et al., Targeting Aberrant Epigenetic Networks Mediated by PRMT1 and KDM4C in Acute Myeloid Leukemia, Cheung et al., 2016, Cancer Cell 29, 32-46 Jan. 11, 2016 © 2016 The Authors, http://dx.doi.org/10.1016/j.ccell.2015.12.007.

* cited by examiner (a)

(b)

STORAGE METHOD AND BANKING SYSTEM OF NT CELL

TECHNICAL FIELD

The present disclosure relates to a method of storing cells prepared using somatic cell nuclear transfer (NT) technology with homozygous genotypes of genes of human leukocyte antigen (HLA)-A, HLA-B, HLA-DR, or the like, and a banking system of the cells.

BACKGROUND ART

Cell therapeutics is a field emerging as a new paradigm in medicine to enable 'fundamental treatment' with cells, and in particular, stem cells, of diseases thought to be treated in a limited manner by drugs or surgical surgeries. In particular, this is a new technical field for fighting disease, enabling functional recovery of tissues and organs that are damaged or functionally degraded from aging, illnesses, accidents, and the like, through regeneration or replacement, and is emerging in the regenerative medicine field as an alternative treatment of intractable diseases.

However, for wider use of cell therapeutics, the complex problem of immune rejection must be solved. Causes of immune rejection are six HLA (HLA-A, HLA-B, HLA-C, HLA-DP, HLA-DQ, HLA-DR) cell surface proteins known as the major histocompatibility antigen complex (MHC). A total of 6 pairs of the HLA genes, including 6 species from paternal genes and 6 species from maternal genes, are expressed in humans. Normal somatic cells express only three pairs in total of HLA-A, HLA-B, and HLA-C which belong to MHC class I, and immune cells express six pairs in total including both MHC class I and MHC class II. A role of HLA surface antigen is to display protein fragments present in cells on cell surfaces, enabling immune cells to detect an infection or mutation in vivo. For this reason, the HLA surface antigen is also called antigen presenting protein.

Somatic cell nuclear transfer (SCNT) technology refers to a technology of replicating a somatic cell through removal of the nucleus of the somatic cell and transplantation of it into an nucleus-removed oocyte, or in other words, generating a stem cell line using a somatic cell, the stem cell line retaining genetic characteristics of the somatic cell, by isolating the nucleus of the somatic cell and injecting the isolated nucleus of the somatic cell into an oocyte from which its nucleus has been removed. This method is advantageous in that an immune rejection response is inhibited due to the use of the patient's own somatic cells, thus enabling patient-specific treatment. Despite the development of NT technology, a rate of formation of a blastocyst from reconstructed oocytes is still low. Therefore, various attempts have been made to increase the blastocyst formation rate. In particular, the biggest obstacle in NT embryos is zygotic gene activation (ZGA), which appears in the 4- to 8-cell stages in large mammals, including humans. To increase the success rate regardless of the variability of donors, it is necessary to eliminate existing epigenetic barriers. In particular, for successful generation of blastocysts from the 2-, 4-, and 8-cell stages, it is necessary to dramatically increase the blastocyst formation success rate by changing the epigenetic state of a donor's nucleus without any defect or loss during the generation.

Therefore, as described above, there is a need for a method of generating cells and a banking system of the cells for use in cell therapeutics for regenerative medical treatment and intractable disease treatment, the cells eliminating immune rejection response, and enabling patient-specific treatment.

DETAILED DESCRIPTION OF THE INVENTION

Technical Problem

The inventors of the present invention have completed the present invention by developing, from homozygous cells, a cell therapeutic or a transplantable cell that does not induce an immune rejection response.

Provided is a method of storing autologous or allogenic NT cell-derived stem cells applicable for the treatment of various diseases.

Provided are a method of generating the NT cell-derived stem cells and a banking system of the NT cell-derived stem cells.

Technical Solution

According to an aspect of the present invention, there is provided a method of storing immunocompatible nuclear transfer (NT) cell-derived stem cells, the method comprising:
  a) screening for homozygosity in a plurality of donor tissues;
  b) isolating nuclei from homozygous cells to generate NT cells;
  c) generating stem cells from the NT cells; and
  d) cryopreserving the stem cells.

According to another aspect of the present invention, there is provided a method of generating immunocompatible nuclear transfer (NT) cell-derived stem cells, the method comprising:
  a) screening for homozygosity in a plurality of donor tissues;
  b) isolating nuclei from homozygous cells to generate NT cells; and
  c) generating stem cells from the NT cells.

According to another aspect of the present invention, there is provided a method of generating differentiated cells from immunocompatible NT cell-derived stem cells, the method comprising:
  a) screening for homozygosity in a plurality of donor tissues;
  b) isolating nuclei from homozygous cells to generate NT cells;
  c) generating stem cells from the NT cells; and
  d) generating differentiated cells for transplantation from the stem cells.

According to another aspect of the present invention, there is provided a banking system of immunocompatible nuclear transfer (NT) cell-derived stem cells, the banking system comprising:
  a means for collecting a plurality of donor tissues;
  a mean for screening the collected donor tissues;
  a mean for generating stem cells from the tissues, and
  a mean for cryopreserving the stem cells.

Advantageous Effects of the Invention

The banking of NT cell-derived stem cells according to one or more embodiments may enable treatment of various diseases or disorders, providing transplantable cells and tissue materials for the treatment of various diseases such as diabetes, osteoarthritis, and Parkinson's disease, and in particular, the possibility of fundamental treatment of cell type-specific defects and a therapeutic approach to reduce risks of immune rejection response and immune tolerance with homozygous cells according to the embodiments.

MODE OF THE INVENTION

Figure 1:
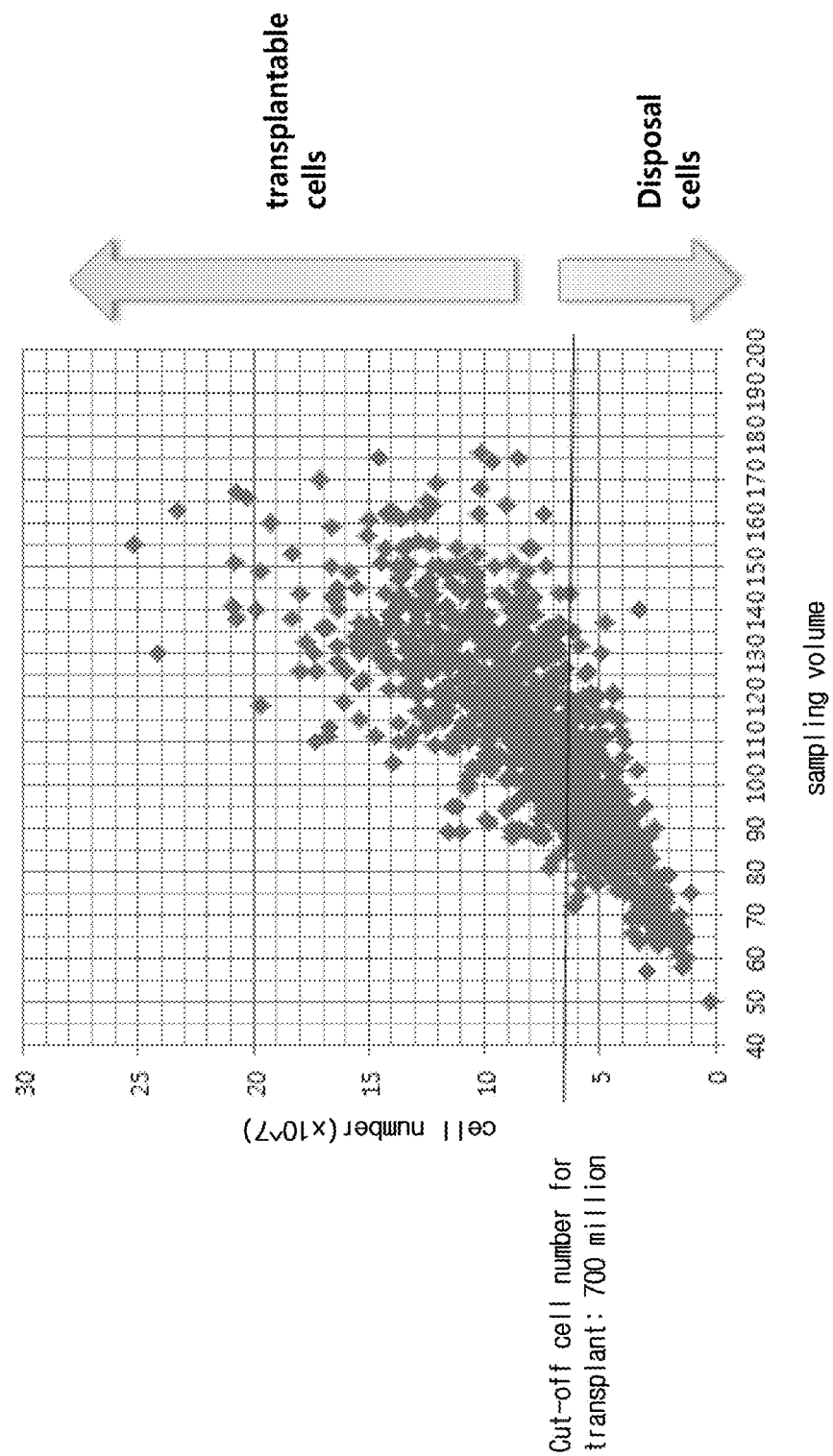
FIG. 1 is a diagram illustrating the classification of cord blood cells into transplantable cells or disposal cells under the current Korean Blood Cord Management and Research Act, which prescribes to discard the cord blood having a cell number less than 700 million or less.

Hereinafter, embodiments will be described in greater detail.

As used herein, the term "immunocompatible antigen homozygosity" may refer to the case where genotypes of each HLA-A, HLA-B, HLA-DR genes inherited from the donor's paternal and maternal lines are completely same, and the donor has three HLA genotypes, not six HLA genotypes.

As used herein, the term "somatic cell" may refer to any tissue cell in the body, except for reproductive (sexual) cells or a precursor thereof.

As used herein, the term "stem cell" may refer to a self-renewal cell (with the ability to undergo multiple cell division cycle progressions while being maintained undifferentiated) having at least one multiple differentiation potential (the capacity to differentiate into at least one specified cells).

As used herein, the term "long-term incubation" may refer to proliferating cells under controlled conditions for a long period of 2 months or more or 10 passages (subcultures) or more. In some embodiments, the long-term incubation may be performed for 4 months or more, 6 months or more, or 1 year or more. In some other embodiments, the long-term incubation may refer to 15 passages or more, 18 passages or more, or 20 passages or more. The duration of the long-term incubation mainly depends on individual cells, and may vary in each cell line.

As used herein, the term "maturation" may refer to a series of harmonious biochemical steps leading to a final differentiated cell.

As used herein, the term "differentiation" may refer to adaptation of a cell to a particular type or a function.

As used herein, the term "differentiated cell" may encompass any somatic cell which is not pluripotent in its original form, as the term is defined herein. Accordingly, the term "differentiated cell" may also encompass a partially differentiated cell, for example, a pluripotent cell, or a stable, non-pluripotent, partially reprogrammed or partially differentiated cell using any composition and method described herein. In some embodiments, the differentiated cell may be a stable, intermediate cell, for example, a non-pluripotent, partially reprogrammed cell. It should be noticed that adding a large number of primary cells in a culture product may cause a slight loss of fully differentiating characteristics. Accordingly, simple incubation of a differentiated or somatic cell does not ensure this cell to become a non-differentiated cell (for example, a undifferentiated cell) or a multipotent cell. Transfer of differentiated cells (including stable, non-pluripotent, partially reprogrammed cell intermediates) to pluripotent cells may require reprogramming stimulus beyond a stimulation level that may cause a partial loss in differentiation characteristics when cells are added to a culture). In some embodiments, reprogrammed, for example, partially reprogrammed cells may be generally grown in extended subcultures without loss of growth potential, compared to parent cells that have a lower probability of generation with the ability of only a limited number of divisions. In some embodiments, the term "differentiated cell" may refer to a further specialized cell (i.e., having a reduced probability of generation) derived from a cell (underwent through intracellular differentiation) of a type (i.e., having an increased probability of generation) of less specialized (for example, from an undifferentiated cell or reprogrammed cell).

In some embodiments, the differentiated cell may be selected from the group consisting of hematopoietic stem cells, myocardial cells, liver cells, chondrocytes, epithelial cells, urinary tract cells, adipocytes, kidney cells, vascular cells, retinal cells, mesenchymal stem cells (MSC), and neuronal cells. However, embodiments are not limited thereto.

The "immunocompatible cells" referred to herein are not specifically limited, and may refer to the cells homozygous for the HLA-A, HLA-B, and HLA-DR genes, and may be transplantable into recipients with any combination of HLA genotypes, having three same genotypes of six pairs.

As used herein, the term "bank" refers to a storage site of stem cells, which may be used, if needed, for the donor herself or other patients as they are or via differentiation for therapeutic, clinical, or research purposes.

As used herein, the term "administration" may refer to introducing a specific substance into a patient in any appropriate manner, for example, via any general route through which the specific substance may reach to a target tissue. For example, the administration may be intraperitoneal administration, intravenous administration, intramuscular administration, subcutaneous administration, intradermal administration, oral administration, topical administration, intranasal administration, intrapulmonary administration, or rectal administration. However, embodiments are not limited thereto. The administration may also be performed with any device that may be reach to a target cell.

In accordance with an aspect of the disclosure, a method of storing immunocompatible nuclear transfer (NT) cell-derived stem cells includes: a) screening for homozygosity in a plurality of donor tissues; b) isolating nuclei from homozygous cells to generate NT cells; c) generating stem cells from the NT cells; and d) cryopreserving the stem cells.

The cells obtained through the NT may carry the nuclear genetic material of the patient, and in this regard, are individual patient-specific. This form of autologous transplantation may allow transplantation of cells into an patient with significantly reduced risk of autologous immune rejection. Furthermore, the homozygous cells as used herein, as cells having a matching HLA antigen type, may be transplantable into an allogenic patient without anti-HLA antibody. That is, the NT-derived stem cells have a homozygous type and may be transplanted into immunocompatible cells.

Thus, in the step a) of screening, cells homozygous for human leukocyte antigen (HLA)-A, HLA-B, and HLA-DR genes may be screened. Reportedly, it will be possible to previously secure immunocompatible cell lines available for transplantation into about 90% or more of the total population of Japan if 140 persons having different immunocompatible homozygosities are found through HLA genotype screening (A more efficient method to generate integration-free human iPS cells, *Nature Methods* 8, 409-412 (2011)).

In one embodiment, primarily homozygous cells were screened based on data from the CHA Public Cord Blood Bank (iCord) in South Korea. According to the current Blood Cord Management and Research Act, cord blood units having a cell number of 700 millions classified as disposal cells may be used for research with the approval of the Cord Blood Committee within the Ministry of Health and Wellfare (see FIG. 1).

Table 1 represents HLA A-B-DRB1 haplotype frequencies in 4,128 umbilical cord blood units (only 0.1% or greater represented, *International Journal of Immunogenetics* (2013) 40: 515-523).

TABLE 1

| RANK | A-B-DRB1 haplotype | HF (%) |
|---|---|---|
| 1 | A * 11.01-g * 44.03-DRB1 * 11.02 | 4.6 |
| 2 | A * 11.01-g * 33.03-DRB1 * 13.01 | 3 |
| 3 | A * 24.02-g * 07.02-DRB1 * 01.01 | 2.73 |
| 4 | A * 11.01-g * 44.03-DRB1 * 07.02 | 2.46 |
| 5 | A * 30.01-g * 23.03-DRB1 * 07.02 | 2.39 |
| 6 | A * 24.07-g * 23.01-DRB1 * 11.07 | 2.1 |
| 7 | A * 11.01-g * 23.01-DRB1 * 04.05 | 1.51 |
| 8 | A * 07.07-g * 45.01-DRB1 * 08.05 | 1.45 |
| 9 | A * 11.01-g * 38.01-DRB1 * 08.05 | 1.35 |
| 10 | A * 14.07-g * 34.01-DRB1 * 04.05 | 1.32 |
| 11 | A * 07.01-g * 27.05-DRB1 * 01.01 | 1.03 |
| 12 | A * 01.02-g * 37.01-DRB1 * 10.01 | 0.91 |
| 13 | A * 24.02-g * 31.01-DRB1 * 09.01 | 0.87 |
| 14 | A * 07.01-g * 23.01-DRB1 * 12.01 | 0.86 |
| 15 | A * 24.02-g * 28.01-DRB1 * 04.01 | 0.77 |
| 16 | A * 10.04-g * 14.01-DRB1 * 04.06 | 0.76 |
| 17 | A * 03.01-g * 44.07-DRB1 * 11.01 | 0.7 |
| 18 | A * 02.01-g * 44.01-DRB1 * 07.01 | 0.54 |
| 19 | A * 29.01-g * 07.03-DRB1 * 03.01 | 0.51 |
| 20 | A * 26.03-g * 13.01-DRB1 * 04.06 | 0.48 |
| 21 | A * 24.03-g * 40.06-DRB1 * 07.01 | 0.46 |
| 22 | A * 24.03-g * 48.01-DRB1 * 08.01 | 0.46 |
| 23 | A * 24.03-g * 13.07-DRB1 * 04.01 | 0.45 |
| 24 | A * 21.01-g * 31.01-DRB1 * 08.02 | 0.44 |
| 25 | A * 11.01-g * 41.01-DRB1 * 46.02 | 0.43 |
| 26 | A * 02.01-g * 34.01-DRB1 * 04.05 | 0.42 |
| 27 | A * 26.03-g * 12.01-DRB1 * 15.01 | 0.41 |
| 28 | A * 02.05-g * 31.01-DRB1 * 12.01 | 0.4 |
| 29 | A * 07.01-g * 17.01-DRB1 * 04.05 | 0.39 |
| 30 | A * 24.07-g * 12.01-DRB1 * 12.07 | 0.38 |
| 31 | A * 02.01-g * 54.01-DRB1 * 1307 | 0.37 |
| 32 | A * 07.05-g * 22.01-DRB1 * 11.01 | 0.37 |
| 33 | A * 24.07-g * 22.01-DRB1 * 15.01 | 0.36 |
| 34 | A * 07.03-g * 32.02-DRB1 * 13.01 | 0.36 |
| 35 | A * 11.01-g * 34.01-DRB1 * 04.05 | 0.36 |
| 36 | A * 11.01-g * 51.01-DRB1 * 13.01 | 0.36 |
| 37 | A * 26.03-g * 15.01-DRB1 * 14.05 | 0.35 |
| 38 | A * 11.01-g * 51.01-DRB1 * 04.05 | 0.33 |
| 39 | A * 26.02-g * 40.06-DRB1 * 09.05 | 0.32 |
| 40 | A * 24.07-g * 21.01-DRB1 * 13.05 | 0.31 |
| 41 | A * 02.01-g * 13.01-DRB1 * 11.05 | 0.3 |
| 42 | A * 02.01-g * 40.01-DRB1 * 11.02 | 0.3 |
| 43 | A * 14.01-g * 40.01-DRB1 * 09.01 | 0.29 |
| 44 | A * 01.05-g * 13.01-DRB1 * 04.05 | 0.29 |
| 45 | A * 01.01-g * 33.03-DRB1 * 07.01 | 0.29 |
| 46 | A * 11.01-g * 31.01-DRB1 * 09.01 | 0.29 |
| 47 | A * 02.01-g * 48.01-DRB1 * 12.01 | 0.28 |
| 48 | A * 02.01-g * 34.01-DRB1 * 08.01 | 0.28 |
| 49 | A * 02.01-g * 13.11-DRB1 * 13.01 | 0.27 |
| 50 | A * 07.01-g * 42.01-DRB1 * 09.01 | 0.27 |
| 51 | A * 07.05-g * 34.01-DRB1 * 13.01 | 0.27 |
| 52 | A * 07.05-g * 19.01-DRB1 * 04.05 | 0.27 |
| 53 | A * 14.07-g * 49.01-DRB1 * 11.01 | 0.26 |
| 54 | A * 02.01-g * 33.01-DRB1 * 07.01 | 0.26 |
| 55 | A * 07.06-g * 40.04-DRB1 * 09.01 | 0.26 |
| 56 | A * 11.01-g * 13.01-DRB1 * 12.07 | 0.26 |
| 57 | A * 02.06-g * 13.01-DRB1 * 13.01 | 0.25 |
| 58 | A * 12.01-g * 44.03-DRB1 * 04.02 | 0.25 |
| 59 | A * 07.01-g * 13.01-DRB1 * 11.01 | 0.24 |
| 60 | A * 07.05-g * 27.03-DRB1 * 01.01 | 0.24 |
| 61 | A * 24.07-g * 21.01-DRB1 * 11.01 | 0.24 |
| 62 | A * 02.01-g * 42.02-DRB1 * 08.01 | 0.23 |
| 63 | A * 11.01-g * 40.05-DRB1 * 08.01 | 0.23 |
| 64 | A * 02.01-g * 15.01-DRB1 * 17.01 | 0.22 |
| 65 | A * 07.01-g * 27.01-DRB1 * 10.01 | 0.22 |
| 66 | A * 24.07-g * 13.01-DRB1 * 13.01 | 0.22 |
| 67 | A * 14.07-g * 40.01-DRB1 * 13.01 | 0.21 |
| 68 | A * 14.01-g * 51.01-DRB1 * 14.03 | 0.21 |
| 69 | A * 14.01-g * 54.01-DRB1 * 03.03 | 0.21 |
| 70 | A * 07.10-g * 40.06-DRB1 * 12.01 | 0.21 |
| 71 | A * 03.03-g * 02.01-DRB1 * 01.01 | 0.21 |
| 72 | A * 11.01-g * 45.01-DRB1 * 03.01 | 0.21 |
| 73 | A * 07.01-g * 13.11-DRB1 * 01.01 | 0.2 |
| 74 | A * 02.01-g * 43.01-DRB1 * 09.01 | 0.2 |
| 75 | A * 24.07-g * 45.01-DRB1 * 04.05 | 0.2 |
| 76 | A * 02.06-g * 21.01-DRB1 * 04.05 | 0.2 |
| 77 | A * 24.01-g * 43.01-DRB1 * 14.54 | 0.2 |
| 78 | A * 24.07-g * 27.01-DRB1 * 05.03 | 0.2 |
| 79 | A * 30.04-g * 14.01-DRB1 * 03.07 | 0.2 |
| 80 | A * 02.01-g * 13.11-DRB1 * 07.01 | 0.19 |
| 81 | A * 07.01-g * 40.01-DRB1 * 14.03 | 0.19 |
| 82 | A * 07.01-g * 40.06-DRB1 * 07.01 | 0.19 |
| 83 | A * 24.03-g * 54.01-DRB1 * 09.01 | 0.19 |
| 84 | A * 26.01-g * 33.01-DRB1 * 04.10 | 0.19 |
| 85 | A * 31.01-g * 58.01-DRB1 * 11.01 | 0.19 |
| 86 | A * 02.01-g * 48.01-DRB1 * 03.03 | 0.18 |
| 87 | A * 02.01-g * 31.01-DRB1 * 13.01 | 0.18 |
| 88 | A * 07.05-g * 31.01-DRB1 * 09.01 | 0.28 |
| 89 | A * 14.07-g * 43.01-DRB1 * 09.01 | 0.27 |
| 90 | A * 01.01-g * 37.01-DRB1 * 07.01 | 0.17 |
| 91 | A * 11.01-g * 48.01-DRB1 * 01.01 | 0.17 |
| 92 | A * 11.01-g * 48.01-DRB1 * 14.03 | 0.17 |
| 93 | A * 11.01-g * 60.01-DRB1 * 11.01 | 0.17 |
| 94 | A * 11.01-g * 31.01-DRB1 * 16.07 | 0.17 |
| 95 | A * 02.05-g * 07.07-DRB1 * 01.01 | 0.16 |
| 96 | A * 02.05-g * 48.01-DRB1 * 09.01 | 0.16 |
| 97 | A * 02.05-g * 51.01-DRB1 * 04.03 | 0.16 |
| 98 | A * 02.05-g * 51.01-DRB1 * 13.01 | 0.16 |
| 99 | A * 24.03-g * 28.01-DRB1 * 13.03 | 0.16 |
| 100 | A * 26.01-g * 40.06-DRB1 * 09.01 | 0.16 |
| 101 | A * 30.01-g * 47.01-DRB1 * 11.01 | 0.26 |
| 102 | A * 11.01-g * 15.02-DRB1 * 13.03 | 0.26 |
| 103 | A * 31.01-g * 07.02-DRB1 * 01.01 | 0.26 |
| 104 | A * 13.01-g * 44.02-DRB1 * 12.01 | 0.26 |
| 105 | A * 07.01-g * 07.02-DRB1 * 01.01 | 0.25 |
| 106 | A * 02.01-g * 35.01-DRB1 * 04.03 | 0.25 |

TABLE 1-continued

| RANK | A-B-DRB1 haplotype | HF (%) |
|---|---|---|
| 107 | A * 24.02-g * 35.01-DRB1 * 11.01 | 0.25 |
| 108 | A * 24.01-g * 15.37-DRB1 * 04.06 | 0.25 |
| 109 | A * 03.01-g * 48.01-DRB1 * 11.01 | 0.25 |
| 110 | A * 10.01-g * 18.02-DRB1 * 04.05 | 0.25 |
| 111 | A * 11.01-g * 44.07-DRB1 * 11.1 | 0.23 |
| 112 | A * 31.01-g * 31.01-DRB1 * 03.03 | 0.23 |
| 113 | A * 31.01-g * 31.01-DRB1 * 13.02 | 0.23 |
| 114 | A * 02.01-g * 13.01-DRB1 * 04.03 | 0.14 |
| 115 | A * 02.01-g * 13.18-DRB1 * 04.02 | 0.14 |
| 116 | A * 24.03-g * 40.02-DRB1 * 18.01 | 0.14 |
| 117 | A * 24.03-g * 40.02-DRB1 * 12.01 | 0.14 |
| 118 | A * 24.03-g * 40.05-DRB1 * 12.01 | 0.14 |
| 119 | A * 24.03-g * 21.01-DRB1 * 12.01 | 0.14 |
| 120 | A * 24.02-g * 35.02-DRB1 * 08.03 | 0.14 |
| 121 | A * 11.01-g * 19.01-DRB1 * 08.03 | 0.14 |
| 122 | A * 11.01-g * 40.01-DRB1 * 08.03 | 0.14 |
| 123 | A * 07.01-g * 35.01-DRB1 * 09.01 | 0.13 |
| 124 | A * 02.01-g * 44.03-DRB1 * 18.03 | 0.13 |
| 125 | A * 11.01-g * 10.04-DRB1 * 04.03 | 0.13 |
| 126 | A * 24.02-g * 40.02-DRB1 * 09.01 | 0.13 |
| 127 | A * 07.01-g * 48.01-DRB1 * 14.34 | 0.13 |
| 128 | A * 02.03-g * 45.01-DRB1 * 08.03 | 0.13 |
| 129 | A * 11.01-g * 13.07-DRB1 * 04.03 | 0.13 |
| 130 | A * 11.01-g * 40.01-DRB1 * 13.01 | 0.13 |
| 131 | A * 11.03-g * 51.01-DRB1 * 14.14 | 0.13 |
| 132 | A * 11.03-g * 40.03-DRB1 * 14.03 | 0.13 |
| 133 | A * 11.03-g * 48.01-DRB1 * 03.03 | 0.13 |
| 134 | A * 01.01-g * 04.01-DRB1 * 03.01 | 0.12 |
| 135 | A * 07.01-g * 19.01-DRB1 * 08.03 | 0.12 |
| 136 | A * 07.01-g * 40.01-DRB1 * 08.03 | 0.12 |
| 137 | A * 24.02-g * 13.02-DRB1 * 07.03 | 0.12 |
| 138 | A * 24.02-g * 13.18-DRB1 * 13.01 | 0.12 |
| 139 | A * 24.02-g * 19.01-DRB1 * 03.03 | 0.12 |
| 140 | A * 07.01-g * 31.01-DRB1 * 04.03 | 0.12 |
| 141 | A * 02.01-g * 31.01-DRB1 * 08.03 | 0.12 |
| 142 | A * 02.06-g * 13.41-DRB1 * 17.02 | 0.12 |
| 143 | A * 07.05-g * 35.01-DRB1 * 09.02 | 0.12 |
| 144 | A * 07.05-g * 40.01-DRB1 * 04.03 | 0.12 |
| 145 | A * 07.05-g * 48.01-DRB1 * 13.41 | 0.12 |
| 146 | A * 24.01-g * 13.01-DRB1 * 04.06 | 0.12 |
| 147 | A * 26.01-g * 27.05-DRB1 * 01.03 | 0.12 |
| 148 | A * 25.01-g * 40.07-DRB1 * 07.01 | 0.12 |
| 149 | A * 20.01-g * 11.07-DRB1 * 17.07 | 0.12 |
| 150 | A * 02.01-g * 40.01-DRB1 * 04.43 | 0.12 |
| 151 | A * 02.01-g * 40.02-DRB1 * 13.01 | 0.11 |
| 152 | A * 24.02-g * 12.01-DRB1 * 07.01 | 0.11 |
| 153 | A * 24.02-g * 22.01-DRB1 * 12.01 | 0.11 |
| 154 | A * 24.02-g * 40.04-DRB1 * 02.01 | 0.11 |
| 155 | A * 02.05-g * 48.01-DRB1 * 04.01 | 0.11 |
| 156 | A * 02.05-g * 31.01-DRB1 * 14.34 | 0.11 |
| 157 | A * 02.05-g * 31.01-DRB1 * 14.03 | 0.11 |
| 158 | A * 24.02-g * 48.01-DRB1 * 13.01 | 0.11 |
| 159 | A * 24.02-g * 48.02-DRB1 * 08.01 | 0.11 |
| 160 | A * 02.05-g * 34.01-DRB1 * 08.03 | 0.11 |
| 161 | A * 07.07-g * 65.01-DRB1 * 17.02 | 0.11 |
| 162 | A * 11.01-g * 07.03-DRB1 * 01.01 | 0.11 |
| 163 | A * 11.01-g * 31.01-DRB1 * 14.01 | 0.11 |
| 164 | A * 11.01-g * 31.01-DRB1 * 13.01 | 0.11 |
| 165 | A * 11.01-g * 44.03-DRB1 * 09.01 | 0.11 |
| 166 | A * 11.01-g * 38.01-DRB1 * 03.03 | 0.11 |
| 167 | A * 07.01-g * 13.01-DRB1 * 07.01 | 0.1 |
| 168 | A * 07.01-g * 13.12-DRB1 * 04.03 | 0.1 |
| 169 | A * 07.01-g * 40.02-DRB1 * 03.03 | 0.1 |
| 170 | A * 24.07-g * 33.04-DRB1 * 03.01 | 0.1 |
| 171 | A * 24.07-g * 33.01-DRB1 * 04.10 | 0.1 |
| 172 | A * 24.07-g * 33.01-DRB1 * 02.01 | 0.1 |
| 173 | A * 24.07-g * 40.01-DRB1 * 14.03 | 0.1 |
| 174 | A * 24.07-g * 40.02-DRB1 * 04.03 | 0.1 |
| 175 | A * 24.07-g * 40.02-DRB1 * 09.03 | 0.1 |
| 176 | A * 24.07-g * 40.02-DRB1 * 12.01 | 0.1 |
| 177 | A * 03.01-g * 48.01-DRB1 * 14.05 | 0.1 |
| 178 | A * 02.05-g * 23.01-DRB1 * 06.07 | 0.1 |
| 179 | A * 02.05-g * 23.01-DRB1 * 12.01 | 0.1 |
| 180 | A * 07.05-g * 43.01-DRB1 * 14.03 | 0.1 |
| 181 | A * 02.05-g * 34.01-DRB1 * 04.03 | 0.1 |
| 182 | A * 24.02-g * 45.01-DRB1 * 09.01 | 0.1 |
| 183 | A * 24.02-g * 31.03-DRB1 * 08.03 | 0.1 |
| 184 | A * 24.02-g * 34.01-DRB1 * 13.01 | 0.1 |
| 185 | A * 24.01-g * 40.02-DRB1 * 13.01 | 0.1 |
| 186 | A * 11.01-g * 33.01-DRB1 * 04.07 | 0.1 |
| 187 | A * 11.01-g * 44.03-DRB1 * 11.07 | 0.1 |
| 188 | A * 11.01-g * 34.01-DRB1 * 03.03 | 0.1 |
| 189 | A * 11.01-g * 11.01-DRB1 * 12.03 | 0.1 |
| 190 | A * 11.01-g * 13.38-DRB1 * 11.01 | 0.1 |
| 191 | A * 11.01-g * 31.01-DRB1 * 11.01 | 0.1 |
| 192 | A * 11.03-g * 44.01-DRB1 * 04.05 | 0.1 |
| 193 | A * 11.03-g * 33.01-DRB1 * 01.01 | 0.1 |

Accordingly, as cells for the present research, primarily frozen umbilical cord bloods (having a cell number less than 700 million) suitable for research may be used. In addition to these cells, any donate cord bloods for research registered in the Korean Network for Organ Sharing (KONOS) may also be used. Further to this, samples collected in the hematopoietic stem cell donor network and CHA hospital-affiliated medical institutions may also be used.

In some embodiments, the step b) of generating NT cells may include: enucleating oocytes; fusing nuclei of somatic cells to the enucleated oocytes; and culturing the fused oocytes in a post-activation medium.

In some embodiments, the method of preparing NT-derived stem cells may include enucleating oocytes; adding at least one nucleus of at least one donor cell to generate NT oocytes; incubating the NT oocytes in an activation medium to activate the NT oocytes; and generating blastocysts from the activated NT oocytes.

In other embodiments, enucleating an oocyte includes removal of a metaphase II (Mil) stage egg spindle. In various embodiments, the first polar body (IPBE) is removed. In another embodiment, the method includes denuding the cumulus cells before the completion of maturation. In one embodiment, the oocyte is monitored with real-time, non-UV light based monitoring for IPBE. In another embodiment, the monitoring occurs in the absence of a staining or labeling agent, such as Hoechst staining. In one embodiment, this includes use of a poloscope, such as a Research Instruments (CRi) Oosight™ imaging system. For example, this can include visualizing the zona pellucida and the spindle complex in the '5 harvested Mil oocyte harvested with 545 nm polarized light. In another embodiment, enucleating an oocyte includes use of a contoured micropipette allows for both puncture of an oocyte membrane and removal of a IPBE from the oocyte. In another embodiment, enucleating an oocyte includes use of a piezoelectric drill. In other embodiments, enucleation is performed in a enucleation medium containing cytochalasin B and optionally, a protein phosphatase inhibitor such as caffeine.

Caffeine as a protein phosphatase inhibitor may inhibit premature activation to improve growth of cloned embryos, and consequently increase blastocyst formation rate. Accordingly, the enucleating of the oocytes may be performed in a medium containing a protein phosphatase inhibitor. The protein phosphatase inhibitor may be caffeine.

In some other embodiments, the adding of at least one nucleus of at least one donor cell to generate the NT oocytes may include transplanting at least one donor nucleus.

Transfer of a donor nucleus may include use of an agent that alters oocyte cell membrane. In one embodiment, enucleating an oocyte trough use of an agent that alters oocyte cell membrane structure includes fusion with a somatic cell. For example, transfer of a donor nucleus may include providing 3-4 donation cells an injection ">pipette (e.g., 12 um diameter), expelling donation cells in a quantity of solution containing a paramyxovirus or paramyxovirus protein, such as Sendai virus envelope protein. This is followed by retrieving the cells using the injection pipette with a distance (4-5 cell length) separating the donation cells arranged linearly, holding an oocyte with a holding pipette, advancing the injection pipette with donation cells into the oocyte. In various embodiments, advancing the injection pipette includes no disruption of the oolema plasma membrane, and insertion of one nuclear donation cell in the perivitelline space, the space between the zona pellucida and the cell membrane, of an oocyte to contact the nuclear donation cells with the oolema plasma membrane, which sits beneath the zona pellucida. In various embodiments, withdrawal of the pipette does not disturb contact between oolema and donation cell. In various embodiments, the oocytes are further incubated. In various embodiments, the cells are fused 1, 2, 3, 4, 5, 6, 7, 8, 9, 10, 11, 12, 13, 14, 15 or more minutes after the donation cell insertion. In various embodiments, the cells are fused 10 min after the donation cell insertion. Optionally, the above procedures are repeated for cells not successfully fused. In various embodiments, a poloscope, such as Oosight™ imaging system, is used throughout the process.

In some embodiment, transplanting a donor nucleus is performed by direct injection. In one embodiment, transfer of a donor nucleus may include electrical cell manipulation, such as electrofusion. In other embodiments, the method may include isolating the nucleus of a somatic nuclear donor, stem cell nuclear donor, and germ cell nuclear donor. In other embodiments, the method may include isolating a somatic nucleus for SCNT, followed by injection of one or more donor nuclei via pipette or piezoelectric injection. In various embodiments, the donor nuclei is from cells such as skin fibroblasts, white blood cells, hair follicles, or any other somatic cell nuclear donor. In another embodiment, the present invention describes a method including isolation and preparation of a nucleus from a germ cell donor. In different embodiments, isolation of a nucleus includes a tissue biopsy, blood draw, or other means of obtaining a tissue sample, processing this tissue with mechanical disassociation, collagenase digestion, washing, centrifuge-based density gradient separation, and/or culturing with standard culture medium.

In some embodiments, the fusing of the nuclei of the somatic cells may be performed in a medium containing Sendai virus or a Sendai virus extract.

After the fusing of the nucleic of somatic cells to the enucleated oocytes, the fused oocytes may be moved into a post-activation medium and then activated.

In some embodiments, the step c) of generating the stem cells from the NT cells may include: incubating the NT oocytes in an activation medium to activate the NT oocytes; generating blastocysts from the activated NT oocytes; and isolating inner cell mass (ICM) cells from the blastocysts. The ICM cells as nuclear transfer human pluripotent stem cell lines (NT-hPSC) may further be cultured.

The activation of the oocytes (artificial oocyte activation) relies on mimicking calcium signaling changes that occur during natural sperm fertilization.

Normal oocyte development relies on high levels of metaphase promoting factor (MPF) activity to arrest oocytes at the metaphase II (MiI) stage. Arrest of the MiI oocyte is disrupted by changes in intracellular calcium ion ($Ca^{2+}$) levels due to sperm entry. This is followed by targeted degradation of cyclin B (a MPF regulatory subunit), which releases the oocyte from arrest, pronuclei formation, and the initiation of meiotic and mitotic processes.

Oocyte activation relies on artificial calcium-alteration strategies to release a cultured oocyte from arrest. Examples include addition of calcium ionophores, lipid-soluble molecules that transport ions across the lipid bilayer, such as ionomycin and A23817. Alternative strategies rely on electrical activation, or direct injection of ions.

As related to NT, reconstruction of a nuclear transferred (i.e., reconstructed) oocyte is also followed by oocyte activation using calcium alteration techniques.

For example, while it has been reported that addition of protein phosphatase inhibitor caffeine to sheep oocytes increases the activity of maturation-promoting factor (MPF) and mitogen-activated protein kinases (MAPKs) and similar benefits have been reported in monkey oocytes, the frequency of blastocyst formation is not enhanced. Further, calcium activation via calcium ionophore, electrical activation, or directO injection does not produce the same timing, spatial regulation, or duration of calcium oscillations as natural fertilization. Adding further complexity is that the effect on calcium also appears to be species specific. In some instances, the use of additional treatment with kinase inhibitors like 6-diemthylaminopurine (6-DMAP), ethanol, and protein synthesis inhibitors like cycloheximide (CHX) are used to enhance MPF inactivation.

Histone deacetylase inhibitors such as TAS are associated with improved NT reprogramming. The treatment with TSA may promote the formation of blastocysts.

In some embodiments, electric pulses may be applied during the somatic cell nuclear fusion and the activation process. Electrical activation may involve electrical pulses in an electrofusion medium. In some embodiments, the electrofusion medium may include 0.1 to 0.5 M mannitol, 0.01 to 1 mM $MgSO_4.7H_2O$, 0.01 to 1 mg/ml polyvinyl alcohol, 1 to 10 mg/ml human serum albumin, and 0.005 to 0.5 mM $CaCl_2.2H_2O$. In some other embodiments, the electrofusion medium may include 0.3 M mannitol, 0.1 mM $MgSO_4.7H_2O$, 0.1 mg/ml polyvinyl alcohol, 3 mg/ml human serum albumin, and 0.05 mM $CaCl_2.2H_2O$.

In various embodiments, the nuclear transfer (NT) oocytes are treated in post-activation medium to complete activation. In different embodiments, activated reconstructed nuclear transferred oocytes are then incubated in post-activation medium. In different embodiments, the post-activation medium is a HEPES-free medium, protein-free medium, GI or G2 medium, cleavage medium, cleavage assist medium, IVF medium, blastocyst formation medium, or global human embryo culture medium. In different embodiments, the post-activation medium includes 6-DMAP, puromycin, ethanol, cycloheximide (CHX), trichostatin A (TSA), and/or cytochalasin B (CB). In different embodiments, the activated oocytes are incubation in the post-activation medium for less than 30, 30-45, 45-60, 60-90, 90-120, 120-150, 150-180, 180-210, 210-240, 240-270, 300-330, 330-360, 360-390, or more than 390 minutes. In certain embodiments, the activated oocytes are incubated for 240, 300, or 360 minutes. In various embodiments, activation and post-activation steps are performed under reduced oxygen conditions. In certain embodiments, reduced oxygen conditions include about 80-85%, 85-90%. 90-95%, 95% or more $N_2$, about 1%, 2%, 3%, 4%, 5%, 6%, 7%, 8%, 9%, 10% or more $O_2$, and about 1%, 2%, 3%, 4%, 5%, 6%, 7%, 8%, 9%, or 10% or more $CO_2$. In certain embodiments, reduced oxygen conditions include about 90% $N_2$, about 5% $O_2$, and about 5% $CO_2$. In various embodiments, the post-activation medium includes 1, 2, 3, 4, 5, 5 or more mM 6-DMAP in cleavage medium for 1, 2, 3, 4, 5, 5 or more hours, incubated in a temperature such as 37° C. in a gas mixture, such about 90% $N_2$, about 5% $O_2$, and about 5% $CO_2$.

After incubation in post-activation medium, the post-activated oocytes are incubated in a wash medium. In different embodiments, the wash medium is a HEPES-free medium, protein-free medium, GI or G2 medium, cleavage medium, cleavage assist medium, IVF medium, blastocyst formation medium. In another embodiment, the culture medium does not require serial medium change, such as global human embryo culture medium. In certain embodiments, the wash medium includes TSA. In certain embodiments, the post-activated oocytes are incubated in the wash medium including TSA for 240, 300, or 360 minutes. In one embodiment, the post-activated reconstructed nuclear transferred oocyte is washed, and further cultured. In one embodiment, the post-activated reconstructed nuclear transferred oocyte washed in a 6-DMAP free medium. In other embodiments the various described media, such as HEPES-free medium, protein-free medium, GI or G2 medium, cleavage medium, cleavage assist medium, IVF medium, blastocyst formation medium, or global human embryo culture medium optionally includes a growth factor such as GM-CSF or IGF1. In various embodiments, the growth factor can be added 1, 2, 3, 4, 5, 6, 7 or more days after nuclear transfer.

In another embodiment, activation and/or post-activation steps includes addition of factors isolated from sperm, derivatives and extracts thereof. In one embodiment, human sperm factors are injected into the activated reconstructed eggs using any of the described injection methods. In one embodiment, human sperm factors are injected into the post-activated reconstructed eggs using any of the described injection methods. In various embodiments, after about one, two, three, or four days, the post-activated reconstructed nuclear transferred oocyte is switched to cleavage medium. In a certain embodiment, after about one day post-activated the reconstructed nuclear transferred oocyte is switched to cleavage medium. In various embodiments, sperm factors include for example, factors from isolating cell proteins present inside or outside of sperm cells. In one embodiment, whole sperm extracts are obtained using detergents and mechanical blending of ejaculated sperm. In another embodiment, whole sperm cell extracts are treated with DNAase I and RNAase. In another embodiment, the crude extract is washed in buffer and centrifugation (20,000 g for 2 hours). In other embodiments, fresh ejaculated human sperm is collected and centrifuge at 900 g for 10 min to remove seminal plasma, followed by resuspension of pellet in Sperm-TALP containing 5 mg/mL bovine serum albumin, and centrifuged at the same setting, followed by removal of supernatant and resuspension of the pellet to a final concentration of $20 \times 10^8$ sperm/mL in nuclear isolation medium ((NIM: 125 mM KCl, 2.6 mM NaCl, 7.8 raM Na2HPO4, 1.4 mM KH2P04, 3.0 mM EDTA disodium salt; pH 7.45 and centrifuged to remove Sperm-TALP. After Sperm-TALP is removed, resuspension of the pellet to the same volume with NIM containing 1 mM dithiothreitol, 100 mM leupeptin, 100 mM antipain, and 100 mg=mL soybean trypsin inhibitor is followed by four cycles of freezing (5 min per cycle in liquid N2) and thawing (5 min per cycle at 15° C.), with compact sperm pellet formation at 20,000× for 50 min at 2° C. Finally, the resulting supernatant is carefully removed, aliquoted, and kept at −80° C. until use.

In various embodiments, the post-activated reconstructed nuclear transferred oocyte is further cultured into a blastocyst. In one embodiment, the post-activated reconstructed nuclear transferred oocyte is further cultured in SAGE cleavage medium, such as Quinn's medium. In another embodiment, the medium promotes pluripotency, such as 3i medium (Neuro basal medium 50%, DMEM/F-12 50%, N2 supplement 1/200 v/v, B27 supplement 1/100 v/v, 100 mM L-glutamine 1/100 v/v, 0.1M B-ME 1/1000 v/v, SU5402 (FGFR inhibitor) 2 µM, PDI 84352 (ERK cascade inhibitor) 0.8 µM, CHIR99021 (GSK3 inhibitor) 3 µM) or modified 3i medium (including PD0325901 (MAPK inhibitor) 0.4 µM). In one embodiment, the further culturing is for 1, 2, 3, 4, 5, 5 or more days. In one embodiment, additional culturing is provided in a culture medium with reprogramming factors and/or methylation-altering agents. In various embodiments, the additional culturing is in G2 medium supplemented with CARM1 and/or Esrrb) for 3 days. For example, CARM1 and/or Esrrb can each be provided at a concentration in the medium of 0.5, 1, 1.5, 2, 2.5, 3, 3.5, 4, 4.5, 5 or more µg/ml. In some embodiments, CARM1 and/or Esrrb are each provided at a concentration in the medium at 2 µg/ml.

In various embodiments, further culturing into a blastocyst and derivation of pluripotent stem cells (pSCs) from the blastocyst includes treat a cultured blastocyst with acidic Tyrode's solution to remove zona pellucida (ZP). In various embodiments, treatment is for a few (e.g., 1-5) seconds. In various embodiments, removal of the ZP is followed by wash in Hepes-HTF medium. In various embodiments, isolation of the inner cell mass (ICM) includes discarding trophoblast of the blastocyst. In various embodiments, the ICM cells are plated mouse embryonic feeders (MEFs) which are prepared one day before the plating. In some embodiments, whole blastocysts are plated on MEFs. For example, this method includes denuding the zona pellucida of the blastocyst. In various embodiments, the method includes removal of the zona pellucida of blastocysts with 0.05, 0.1, 0.2, 0.3, 0.4, 0.5, 0.6, 0.7, 0.8, 0.9, or 1% pronase in Hepes-HTF medium. In one embodiment, the method includes removal of the zonae pellucida of blastocysts with 0.5% pronase in Hepes-HTF medium. In another embodiment, the method includes application of pronase in TH3 (SAGE Blastocyst medium), medium for 1-10, 10-20, 20-30, 30-60, 60-120, 120-180, or >180 seconds. In another embodiment, the method includes application of 0.5% pronase in HTF medium for 30-60 seconds. In one embodiment, the blastocyst is derived from a parthenote obtained from parthenogenesis of an oocyte. In one embodiment, the hPSC line is a parthenote-derived human pluripotent hPSC (pn-hPSC) cell line. In another embodiment, the blastocyst is derived from a reconstructed nuclear transferred oocyte obtained from somatic cell nuclear transfer (SCNT) of a donation cell nucleus into a recipient oocyte. In one embodiment, the hPSC line is a somatic cell nuclear transfer human pluripotent hPSC (NT-hPSC) cell line.

In another embodiment, the present invention describes a method of immunesurgery, including mechanical dispersion of the inner cell mass (ICM) from trophectodermal cells. In various embodiments, a denuded blastocyst is treated with rabbit anti-human spleen serum for about 10, 20, 25, 30, 35, 40, 45, or 60 minutes at 37° C. In one embodiment, a denuded blastocyst is treated with rabbit anti-human spleen serum for about 30 minutes at 37° C. In one embodiment, the method includes washing the denuded blastocyst with TH3 (SAGE Blastocyst medium), incubation in guinea pig complement reconstructed with HECM-9 (SAGE Blastocyst medium), for 30 min at 37° C. In different embodiments, zonae pellucidae of expanded blastocysts are be removed by brief exposure (45-60 seconds) to 0.5% pronase or acidic Tyrode's solution in TH3 (hepes-HTF) medium. In one embodiment, the method optionally includes mechanical cell dispersion using small bore pipetting or laser assisted hatching method using Zilos-tk Unit (Hamilton Thorne) to separate inner cell mass cells from the trophoectodermal cells.

In some embodiments, the post-activation medium may be performed in a medium containing TSA. The post-activation medium may contain 6-DMAP. In some other embodiments, during the post-activation, after culturing in a medium containing 6-DMAP, additional culturing in a medium containing TSA may be performed.

In various embodiments, to increase a successful nuclear NT rate, the nuclei of at least one donor cell may be modified by contact with an epigenetic modifying agent. The epigenetic modifying agent may increase transfer efficiency by changing the state of methylation or acetylation of a specific protein or DNA, and consequently increase NT efficiency. A target of the epigenetic modifying agent may include at least one of a histone acetyl transferase (HAT) protein, a histone deacetylase (HDAC) protein, a lysine demethylase (KDM) domain protein, and a protein methyl transferase (PMT) domain protein. These agents may include small interfering RNA (siRNA), small molecules, proteins, peptides, antibodies, and the like. These agents may act on an epigenetic target associated with a reprogramming resistant region. The NT oocytes may be cultured in the presence of such an epigenetic modifying agent. Examples of these agents are represented in Tables 2 to S. Examples of histone acetyl transferase (HAT) proteins, histone deacetylase (HDAC) proteins, lysine demethylase (KDM) domain proteins, and protein methyl transferase (PMT) domain proteins are not limited to those represented in the following tables.

TABLE 2

Histone acetyl transferase (HAT) proteins

| Target_ID (\|domain #) | Full name | Uniprot_ID | NCBI geneid |
|---|---|---|---|
| ATAT1 | alpha tubulin acetyltransferase 1 | Q5SQI0-1 | 79969 |
| CLOCK | clock homolog (mouse) | O15516-1 | 9575 |
| CREBBP | CREB binding protein | Q92793-1 | 1387 |
| ELP3 | elongation protein 3 homolog (*S. cerevisiae*) | Q9H9T3-1 | 55140 |
| EP300 | E1A binding protein p300 | Q09472-1 | 2033 |
| GTF3C4 | general transcription factor IIIC, polypeptide 4, 90 kDa | Q9UKN8-1 | 9329 |
| HAT1 | histone acetyltransferase 1 | O14929-1 | 8520 |
| KAT2A/GCN5L2 | K(lysine) acetyltransferase 2A | Q92830-1 | 2648 |
| KAT2B/PCAF | K(lysine) acetyltransferase 2B | Q92831-1 | 8850 |
| KAT5/TIP60 | K(lysine) acetyltransferase 5 | Q92993-1 | 10524 |
| MYST1 | K(lysine) acetyltransferase 8 | Q9H7Z6-1 | 84148 |
| MYST2 | K(lysine) acetyltransferase 7 | Q95251-1 | 11143 |
| MYST3 | K(lysine) acetyltransferase 6A | Q92794-1 | 7994 |
| MYST4 | K(lysine) acetyltransferase 6B | Q8WYB5-1 | 23522 |
| NCOA1 | nuclear receptor coactivator 1 | Q15788-1 | 8648 |
| NCOA3 | nuclear receptor coactivator 3 | Q9Y6Q9-1 | 8202 |
| TAF1 | TAF1 RNA polymerase II, TATA box binding protein (TBP)-associated factor, 250 kDa | P21675-1 | 6872 |
| TAF1L | TAF1 RNA polymerase II, TATA box binding protein (TBP)-associated factor, 210 kDa-like | Q8IZX4-1 | 138474 |

TABLE 3

Histone deacetylase (HDAC) proteins

| Target_ID (\|domain #) | Full name | Uniprot_ID | NCBI geneid |
|---|---|---|---|
| HDAC1 | histone deacetylase 1 | Q13547_1 | 3065 |
| HDAC10\|1 | histone deacetylase 10 | Q969S8_1 | 83933 |
| HDAC10\|2 | histone deacetylase 10 | Q969S8_1 | 83933 |
| HDAC10\|1 | histone deacetylase 10 | Q969S8_2 | 83933 |
| HDAC10 | histone deacetylase 10 | Q969S8_5 | 83933 |
| HDAC11 | histone deacetylase 11 | Q96DB2_1 | 79885 |
| HDAC2 | histone deacetylase 2 | Q92769_1 | 3066 |
| HDAC3 | histone deacetylase 3 | O15379_1 | 8841 |
| HDAC4 | histone deacetylase 4 | P56524_1 | 9759 |
| HDAC5 | histone deacetylase 5 | Q9UQL6_1 | 10014 |
| HDAC6\|1 | histone deacetylase 6 | Q9UBN7_1 | 10013 |
| HDAC6\|2 | histone deacetylase 6 | Q9UBN7_1 | 10013 |
| HDAC7 | histone deacetylase 7 | Q8WUI4_1 | 51564 |
| HDAC8 | histone deacetylase 8 | Q9BY41_1 | 55869 |
| HDAC9 | histone deacetylase 9 | Q9UKV0_1 | 9734 |
| SIRT1 | sirtuin 1 | Q96EB6_1 | 23411 |
| SIRT2 | sirtuin 2 | Q8IXJ6_1 | 22933 |
| SIRT3 | sirtuin 3 | Q9NTG7_1 | 23410 |
| SIRT4 | sirtuin 4 | Q9Y6E7_1 | 23409 |
| SIRT5 | sirtuin 5 | Q9NXA8_1 | 23408 |
| SIRT6 | sirtuin 6 | Q8N6T7_1 | 51548 |
| SIRT6 | sirtuin 6 | Q8N6T7_2 | 51548 |
| SIRT6 | sirtuin 6 | Q8N6T7_4 | 51548 |
| SIRT7 | sirtuin 7 | Q9NRC8_1 | 51547 |

TABLE 4

Lysine demethylase (KDM) domain proteins

| Target_ID (\|domain #) | Full name | Uniprot_ID | NCBI geneid |
|---|---|---|---|
| JARID2 | jumonji, AT rich interactive domain 2 | Q92833_1 | 3720 |
| JHDM1D | jumonji C domain containing histone demethylase 1 homolog D (*S. cerevisiae*) | Q6ZMT4_1 | 80853 |
| JMJD1C | jumonji domain containing 1C | Q15652_1 | 221037 |
| JMJD5 | jumonji domain containing 5 | Q8N371_1 | 79831 |
| KDM1A | lysine (K)-specific demethylase 1A | O60341_1 | 23028 |
| KDM1B | lysine (K)-specific demethylase 1B | Q8NB78_1 | 221656 |
| KDM1B | lysine (K)-specific demethylase 1B | Q8NB78_2 | 221656 |
| KDM2A | lysine (K)-specific demethylase 2A | Q9Y2K7_1 | 22992 |
| KDM2B | lysine (K)-specific demethylase 2B | Q8NHM5_1 | 84678 |
| KDM3A | lysine (K)-specific demethylase 3A | Q9Y4C1_1 | 55818 |
| KDM3B | lysine (K)-specific demethylase 3B | Q7LBC6_1 | 51780 |
| KDM4A | lysine (K)-specific demethylase 4A | O75164_1 | 9682 |
| KDM4B | lysine (K)-specific demethylase 4B | O94953_1 | 23030 |
| KDM4C | lysine (K)-specific demethylase 4C | Q9H3R0_1 | 23081 |
| KDM4D | lysine (K)-specific demethylase 4D | Q6B0I6_1 | 55693 |
| KDM4DL | lysine (K)-specific demethylase 4D-like | B2RXH2_1 | 390245 |
| KDM5A | lysine (K)-specific demethylase 5A | P29375_1 | 5927 |
| KDM5B | lysine (K)-specific demethylase 5B | Q9UGL1_1 | 10765 |
| KDM5C | lysine (K)-specific demethylase 5C | P41229_1 | 8242 |
| KDM5D | lysine (K)-specific demethylase 5D | Q9BY66_1 | 8284 |
| KDM6A | lysine (K)-specific demethylase 6A | O15550_1 | 7403 |
| KDM6B | lysine (K)-specific demethylase 6B | O15054_1 | 23135 |
| MINA | MYC induced nuclear antigen | Q8IUF8_1 | 84864 |
| NO66 | chromosome 14 open reading frame 169 | Q9H6W3_1 | 79697 |

TABLE 5

Protein methyl transferase (PMT) domain proteins

| Target_ID (\|domain #) | Full name | Uniprot_ID | NCBI geneid |
|---|---|---|---|
| ASH1L | ash1 (absent, small, or homeotic)-like (*Drosophila*) | Q9NR48_1 | 55870 |
| CARM1 | coactivator-associated arginine methyltransferase 1 | Q86X55_1 | 10498 |
| DOT1L | DOT1-like, histone H3 methyltransferase (*S. cerevisiae*) | Q8TEK3_1 | 84444 |
| EHMT1 | euchromatic histone-lysine N-methyltransferase 1 | Q9H9B1_1 | 79813 |
| EHMT2 | euchromatic histone-lysine N-methyltransferase 2 | Q96KQ7_1 | 10919 |
| EZH1 | enhancer of zeste homolog 1 (*Drosophila*) | Q92800_1 | 2145 |
| EZH2 | enhancer of zeste homolog 2 (*Drosophila*) | Q15910_1 | 2146 |
| EZH2 | enhancer of zeste homolog 2 (*Drosophila*) | Q15910_5 | 2146 |
| MDS1 | MDS1 and EVI1 complex locus | Q03112_3 | 2122 |
| MLL | myeloid/lymphoid or mixed-lineage leukemia (trithorax homolog, *Drosophila*) | Q03164_1 | 4297 |
| MLL2 | myeloid/lymphoid or mixed-lineage leukemia 2 | O14686_1 | 8085 |
| MLL3 | myeloid/lymphoid or mixed-lineage leukemia 3 | Q8NEZ4_1 | 58508 |
| MLL4 | — | Q9UMN6_1 | 9757 |
| MLL5 | myeloid/lymphoid or mixed-lineage leukemia 5 (trithorax homolog, *Drosophila*) | Q8IZD2_1 | 55904 |
| NSD1 | nuclear receptor binding SET domain protein 1 | Q96L73_1 | 64324 |
| PRDM1 | PR domain containing 1, with ZNF domain | O75626_1 | 639 |
| PRDM10 | PR domain containing 10 | Q9NQV6_1 | 56980 |
| PRDM11 | PR domain containing 11 | Q9NQV5_1 | 56981 |
| PRDM12 | PR domain containing 12 | Q9H4Q4_1 | 59335 |
| PRDM13 | PR domain containing 13 | Q9H4Q3_1 | 59336 |
| PRDM14 | PR domain containing 14 | Q9GZV8_1 | 63978 |
| PRDM15 | PR domain containing 15 | P57071_1 | 63977 |
| PRDM16 | PR domain containing 16 | Q9HAZ2_1 | 63976 |
| PRDM2 | PR domain containing 2, with ZNF domain | Q13029_1 | 7799 |
| PRDM4 | PR domain containing 4 | Q9UKN5_1 | 11108 |
| PRDM5 | PR domain containing 5 | Q9NQX1_1 | 11107 |
| PRDM6 | PR domain containing 6 | Q9NQX0_1 | 93166 |
| PRDM7 | PR domain containing 7 | Q9NQW5_1 | 11105 |
| PRDM8 | PR domain containing 8 | Q9NQV8_1 | 56978 |
| PRDM9 | PR domain containing 9 | Q9NQV7_1 | 56979 |
| PRMT1 | protein arginine methyltransferase 1 | Q99873_1 | 3276 |
| PRMT2 | protein arginine methyltransferase 2 | P55345_1 | 3275 |
| PRMT3 | protein arginine methyltransferase 3 | O60678_1 | 10196 |

TABLE 5-continued

Protein methyl transferase (PMT) domain proteins

| Target_ID (\|domain #) | Full name | Uniprot_ID | NCBI geneid |
|---|---|---|---|
| PRMT5 | protein arginine methyltransferase 5 | O14744_1 | 10419 |
| PRMT6 | protein arginine methyltransferase 6 | Q96LA8_1 | 55170 |
| PRMT7\|1 | protein arginine methyltransferase 7 | Q9NVM4_1 | 54496 |
| PRMT7\|2 | protein arginine methyltransferase 7 | Q9NVM4_1 | 54496 |
| PRMT8 | protein arginine methyltransferase 8 | Q9NR22_1 | 56341 |
| SETD1A | SET domain containing 1A | O15047_1 | 9739 |
| SETD1B | SET domain containing 1B | Q9UPS6_1 | 23067 |
| SETD2 | SET domain containing 2 | Q9BYW2_1 | 29072 |
| SETD3 | SET domain containing 3 | Q86TU7_1 | 84193 |
| SETD4 | SET domain containing 4 | Q9NVD3_1 | 54093 |
| SETD5 | SET domain containing 5 | Q9C0A6_1 | 55209 |
| SETD6 | SET domain containing 6 | Q8TBK2_1 | 79918 |
| SETD6 | SET domain containing 6 | Q8TBK2_2 | 79918 |
| SETD7 | SET domain containing (lysine methyltransferase) 7 | Q8WTS6_1 | 80854 |
| SETD8 | SET domain containing (lysine methyltransferase) 8 | Q9NQR1_1 | 387893 |
| SETDB1 | SET domain, bifurcated 1 | Q15047_1 | 9869 |
| SETDB2 | SET domain, bifurcated 2 | Q96T68_1 | 83852 |
| SETMAR | SET domain and mariner transposase fusion gene | Q53H47_1 | 6419 |
| SMYD1 | SET and MYND domain containing 1 | Q8NB12_1 | 150572 |
| SMYD2 | SET and MYND domain containing 2 | Q9NRG4_1 | 56950 |
| SMYD3 | SET and MYND domain containing 3 | Q9H7B4_1 | 64754 |
| SMYD4 | SET and MYND domain containing 4 | Q8IYR2_1 | 114826 |
| SMYD5 | SMYD family member 5 | Q6GMV2_1 | 10322 |
| SUV39H1 | suppressor of variegation 3-9 homolog 1 (*Drosophila*) | O43463_1 | 6839 |
| SUV39H2 | suppressor of variegation 3-9 homolog 2 (*Drosophila*) | Q9H5I1_1 | 79723 |
| SUV420H1 | suppressor of variegation 4-20 homolog 1 (*Drosophila*) | Q4FZB7_1 | 51111 |
| SUV420H2 | suppressor of variegation 4-20 homolog 2 (*Drosophila*) | Q86Y97_1 | 84787 |
| WHSC1 | Wolf-Hirschhorn syndrome candidate 1 | O96028_1 | 7468 |
| WHSC1L1 | Wolf-Hirschhorn syndrome candidate 1-like 1 | Q9BZ95_1 | 54904 |

In general, methyltransferases may be inhibited by co-substrate analogues. Three types of co-substrate analogues are known to inhibit various types of methyltransferase: Sinefugin as a structurally similar antibiotic compound to S-adenosylmethionone (SAM), and dimethylated co-substrate SAH and methylthioadenosine as feedback inhibitors. Lysine methyl inhibitors may include chaetocin, the first identified inhibitor, and BIX-01294 as a G9a (KMT1C) inhibitor, which are selective for SUV39H1 and PRM1. The compound BIX-01338, a slightly non-selective inhibitor without selectivity between lysine and arginine methyltransferase, may inhibit G9a with an IC50 of 5 mM and PRMT1 with an IC50 of 6 mM. UNC0224 is a new inhibitor of lysine methyltransferase G9a with an IC50 of 15 mM. Histone methyltransferase inhibitors such as EPZ5676, EPZ005687, and GSK126 also show anticancer activity in various animal cancer models.

Protein arginine methylation may be performed by PRMTs, which are classified into two groups: Type I methyltransferases and Type II methyltransferases. Type I methyltransferases may form asymmetrically substituted arginine residues, while type II methyltransferases may form symmetrically substituted arginine residues. CARM1 shows affinity with proline-glycine-methionine-arginine (so-called PGM motifs). PRMT5 is also known to methylate PGM motifs. Co-substrate analogues such as sinefungin may also be used as arginine methyltransferase inhibitors (also known as AMIs). AMI-1 is the most active inhibitor with an IC50 of 9 mM. Allatodapsone and stilbamidine inhibitors may induce hypomethylation of H4R3.

Another type of epigenetic target may be to increase NT efficiency. DNA methyltransferase (DNMTs) preferentially methylate the CpG nucleotide sequence of DNA. Three mammalian DNA methyltransferases DNMT1, DNMT3A, and DNMT3 have been identified. In general, methylation of these promoter regions may prevent gene expression by interfering with the binding of transcription factors to DNA. In addition, methylated DNA is bound by methyl-CpG binding domain proteins. These proteins may attract histone modeling enzymes and consequently condense chromatin structure, thus inducing a gene expression inhibitory mechanism. DNMT inhibitors may inhibit gene expression suppression, and consequently increase NT efficiency. Examples of DNMT inhibitors include several compounds, including chlorogenic acid, mithramycin, azacytide, bisdemethoxycurcumim, decitabine, lomegutatrib, benzylguanine, sorafenib, and sorafenib tosylate.

In addition, histone deacetylases (HDACs) may remove acetyl groups from N-acetyl lysine amino acid of histone, resulting in histone with more positive charges, thus which are strongly bound to negatively charged DNA. Condensation of the DNA structure and genetic transcription may be further inhibited. HDACs may be divided into four subgroups according to the locations and functions thereof. Class I HDACs (subtypes 1, 2, 3, and 8) are mainly found in the nucleus, and class II HDACs (subtypes 4, 5, 6, 7, 9, and 10) may move through the nuclear membrane and are found in both the nucleus and cytoplasm. Type III HDACs are called silent information regulator 2 (Sir2), and type IV HDACs (subtype 11) are found in both the nucleus and cytoplasm and are mainly located in the brain, heart, and muscle cells. HDACs inhibitors may exhibit anticancer activity when administered in combination with other chemical synthetic drugs. HDAC inhibitors may promote DN transcription and consequently increase NT efficiency.

The post-activation medium may include epigenetic modifying agents, for example, epigenetic chromatin and β histone modification agents, and/or DNA modifiers. In some embodiments, these epigenetic modifying agents may be selected from protein arginine methyl-transferase (PRMT1) and coactivator-associated arginine methyltransferase 1 (CARM1/PRMT4) or orphan nuclear receptor estrogen related receptor β (Esrrb) protein; or may be selected from RNAs or proteins of lysine specific demethylase 4A (Lysine (K)-Specific Demethylase 4A, Kdm4a), lysine specific demethylase 4B (Lysine (K)-Specific Demethylase 4B, Kdm4b), or lysine specific demethylase 4D (Lysine (K)-Specific Demethylase 4D, Kdm4d). In some embodiments, the methylation-altering agents and/or DNA modification are expressed as modified recombinant proteins. For example, CARM1 and Esrrb can be modified with 7× arginine (7R)-cell-penetrating peptides (CPPs), or any other proteins known to one of ordinary skill enhance penetration of proteins and peptides across cellular and nuclear membranes, enhance binding and/or transactivation to DNA. In other embodiments, the method may include epigenetically reprogramming the nuclear donor cells using transcription factor-based reprogramming with octamer binding transcription factor-4 (Oct-4), sex determining region Y-box-2 (Sox-2), nanog, Kruppel-like factor-4 (Klk-4), MyoD, c-Myc, zinc finger protein-42 (Rex-I/Zfp-42), lefty A, teratocarcinoma-derived growth factor (Tdgf), and/or telomeric repeating binding factor (Terf-1). In various embodiments, the method includes direct piezoelectric injection, viral injection, liposomal injection, or other methods of intracytoplasmic injection. In various embodiments, the transcription factors may be delivered in the form of mRNA, protein, and/or cellular extracts that can be applied prior to the nuclear transfer to the enucleated oocyte. In other embodiments, the method may include using HDAC inhibitors (Class I, II, and III), or DNMT3a and DNMT3b inhibitors.

In some embodiments, the post-activation medium may include an epigenetic modifying agent. In some embodiments, the epigenetic modifying agent may be involved in at least one selected from histone acetyl transferase (HAT) proteins, histone deacetylase (HDAC) proteins, lysine demethylase domain proteins, protein methyl transferase (PMT) domain proteins, and DNA methyltransferases (DNMTs). In the method of generating NT cell-derived stem cell, according to one or more embodiments, the step c) of generating the stem cells may include: activating the NT cells and generating blastocysts; isolating inner cell mass (ICM) cells from the generated blastocysts; and further culturing the isolated ICM cells into the stem cells.

In some embodiments, the stem cells may be cryopreserved for future use. In some embodiments, the cryopreserving agent may include at least one cytoprotective agent, including, for example, but not limited to, diemethyl sulfoxide (DMSO), ethylene glycol, glycerol, and propandiol; at least one culture medium, including, but not limited to a DMEM, a MEM, and the above-disclosed patent medium; and a solution including at least one additional material, including, but not limited to, sucrose, dextran, a serum replacement, and a HEPES buffer. The stem cell may be cryopreserved in the solution. In some embodiments, the solution may include a CryoStor® CS-10 medium (BioLife Solutions Inc., Bothell, Washington, U.S.A). In some other embodiments, the serum replacement may be a KnockOut™ Serum Replacement (Invitrogen, Cat No. 10828-028).

The cryopreservation of the generated stem cells may include freezing cells at a controlled rate or freezing in a "manual" mode. The rate-controlled freezing may be initiated by turning on a rate-controlled freezer and setting a tissue or cell freezing program. The rate-controlled freezer may use liquid nitrogen to lower the temperature of an inner chamber (thereby reducing the temperature of any content in the chamber). The cell freezing program may start with cooling the inner chamber to 4° C. and keeping the temperature until it is stimulated to continue the process. While the rate-controlled freezer cooled, cells may be suspended in a cryopreservation medium cooled down to 4° C. 1 ml of the cell suspension is portioned into each cryovial. Then, the cryovial is labeled and then placed into the chamber of the rate-controlled freezer and it is stimulated to continue the operation of the program. First, the temperature of the chamber is maintained at about 4° C. for additional 10 minutes. Next, the chamber is cooled down at a rate of −1° C./min until the temperature of the chamber reaches −80° C. Then, the chamber is cooled down at a rate of −50° C./min until the temperature of the chamber reaches −120° C. After the temperature is maintained at −120° C. for 5 minutes, the temperature of the frozen cells reaches equilibrium at −120° C. Then, the cryovials of the frozen cells are transferred to liquid nitrogen (Dewar) for long-term storage.

In accordance with another aspect of the disclosure, a method of generating immunocompatible NT cell-derived stem cells includes: a) screening for homozygosity in a plurality of donor tissues; b) isolating nuclei from homozygous cells to generate NT cells; and c) generating stem cells from the NT cells.

In some embodiments, in the step a) of screening, the cells homozygous for the human leukocyte antigen (HLA)-A, HLA-B, and HLA-DR genes may be screened. In some embodiments, the step b) of generating the NT cells may include: enucleating oocytes; fusing nuclei of somatic cells to the enucleated oocytes; and culturing the fused oocytes in a post-activation medium. In some other embodiments, the enucleating of the oocytes may be performed in a medium containing a protein phosphatase inhibitor. The fusing of the nuclei of the somatic cells may be performed in a medium containing Sendai virus or a Sendai virus extract. The post-activation medium may include a histone deacetylase inhibitor. For example, the post-activation medium may include TSA. The post-activation medium may include an epigenetic modifying agent. For example, the epigenetic modifying agent may be involved in at least one selected from the group consisting of a histone acetyl transferase (HAT) protein, a histone deacetylase (HDAC) protein, a lysine demethylase (KDM) domain protein, and a protein methyl transferase (PMT) domain protein.

In one or more embodiments, a method of generating differentiated cells from immunocompatible NT cell-derived stem cells includes: a) screening for homozygosity in a plurality of donor tissues; b) isolating nuclei from homozygous cells to generate NT cells; c) generating stem cells from the NT cells; and d) generating the differentiated cells for transplantation from the stem cells.

Optionally, the method may further include, after the step c), cryopreserving the stem cells. In this case, optionally, the method may further include thawing the cryopreserved stem cells before the step d).

The differentiated cells may refer to cells differentiated into at least one selected from the group consisting of, but not limited to, hematopoietic stem cells, myocardial cells, liver cells, chondrocytes, epithelial cells, urinary tract cells, adipocytes, kidney cells, vascular cells, retinal cells, mesenchymal stem cells (MSC), and neuronal cells, and any of the cells used as a therapeutic agent through cell transplantation. The method may further include screening immunocompatible cells through HLA screening of allogenic patients. Immunocompatibility may increase the optimal availability of transplantable material for regenerative therapy, enabling banking of the cells. Such a banking system may reduce the continuous supply of new oocytes through replacement of NT cell generation using autologous cells and also enable a wide range of autologous or heterologous cell transplantation. In particular, the step of cell screening from the banking system for heterologous cell transplantation and the step of generating differentiated cells from the screened stem cells may expand the range of use as a variety of cell therapeutic agents. The present invention may be integrated into the conventional field of cell transplantation therapy in various ways, and may be applied to the various treatment fields of, for example, blood vessel-related diseases through differentiation into vascular endothelial cells, retinal-related diseases through differentiation into retinal pigment epithelial cells, degenerative neuronal diseases through differentiation into nerve cells, and the like. However, embodiments are not limited thereto.

In accordance with aspects of the disclosure, the present invention provides as cell mass including the immunocompatible nuclear transfer (NT) cell-derived stem cells generated by the method according to any of the embodiments, and a composition including the cell mass of the NT cell-derived stem cells for the treatment of various diseases.

In some embodiments, the cell composition may include about 0.1 to 99.9 wt % of the cell as an active ingredient with respect to a total weight of the composition, and may include a pharmaceutically acceptable carrier, an excipient or a diluent.

In some embodiments, the composition may be in any of a variety of oral or parenteral formulations. The composition may be formulated using a commonly used diluent or excipient, for example, filler, an extender, a binder, a wetting agent, a disintegrant, or surfactant. A solid formulation for oral administration may include, for example, a tablet, a pill, powder, granules, or a capsule. These solid formulations may be prepared by mixing at least one compound with at least one excipient, for example, starch, calcium carbonate, sucrose or lactose, gelatin, or the like. In addition to a common excipient, a lubricant such as magnesium stearate, talc, or the like may be used. A liquid formulation for oral administration may be a suspension, a liquid, an emulsion, a syrup, or the like, which may include a variety of excipients, for example, a wetting agent, a sweetener, a flavoring agent, a preservative, or the like, in addition to a common diluent such as water or liquid paraffin. A formulation for parenteral administration may include a sterile aqueous solution, a non-aqueous solvent, a suspension, an emulsion, a freeze-dried preparation, or a suppository. The non-aqueous solvent and a solvent for the suspension may be, for example, propylene glycol, polyethylene glycol, a vegetable oil such as olive oil, or an injectable ester such as ethyl oleate. As suppository bases, witepsol, macrogol, Tween 61, cacao paper, laurin, glycerogelatin, or the like may be used.

The pharmaceutically effective amount may be about 0.0001 to about 100 mg/kg, and in some embodiments, about 0.001 to about 10 mg/kg. However, embodiments are not limited thereto. The amount of administration may vary depending on the body weight, age, sex, health status, diet, administration period, administration method, elimination rate, severity of disease, or the like.

The composition may be orally or parenterally administered. The parenteral administration may be intraperitoneal injection, rectal injection, subcutaneous injection, intravenous injection, intramuscular injection, intrauterine injection, intracerebral injection, or intrathoracic injection. The composition may be used in the form of a general pharmaceutical formulation. The composition may be administered by injection.

The composition according to one or more embodiments may be used alone or in combination with any method of surgery, radiation therapy, hormone therapy, chemotherapy, and using a biologic response modifier.

In accordance with another aspect of the disclosure, a banking system of immunocompatible nuclear transfer (NT) cell-derived stem cells includes: a means for collecting a plurality of donor tissues; a means for screening for immunocompatibility in the collected donor tissues; a means for generating stem cells from immunocompatible tissues, and a means for cryopreserving the stem cells.

The present invention provides a stem cell bank for storing NT cell-derived stem cells obtained from a plurality of individual donors. The stored stem cells may be used as a source of cells for the recovery of a specific cell population of the donor or for the treatment or clinical use for other individuals. The stored stem cells may also be used for research application. The stored stem cells may be used or administered into a patient as they or via differentiation into a specific cells through thawing after long-term storage.

One or more embodiments of the present disclosure will now be described in detail with reference to the following examples. However, these examples are only for illustrative purposes and are not intended to limit the scope of the one or more embodiments of the present disclosure.

Example 1

Screening of Homozygous Cells From Donation Cells and Selection of Donor Cells

Homozygous cells were screened from discarded cord bloods having a cell number less than 700 millions in the CHA Public Cord Blood Bank (iCord) in South Korea. For HLA-A, B, and DRB1 genotyping, after genomic DNA extraction using Gentra Puregene™ Blood Kits (QIAGEN, Hilden, Germany), sequence-based typing was performed using a SeCore A, B and DRB1 Locus Sequencing Kit (Invitrogen, Brown Deer, Wisconsin, USA). In particular, amplification was performed with a kit using exons 2-4 for the HLA-A and -B genes and exon 2 for the HLA-DRB1 gene as locus specific primers, and then resulting PCR products were subjected to sequencing using an ABI3130XL Genetic Analyzer (Applied Biosystems, Foster City, California, USA), and data analysis was performed using a HLA SBT u-type software v3.0 (Invitrogen) and a Sequencher (Gene Codes Corp., Ann Arbor, Michigan, USA). Through these methods, the most frequent (probable) human leukocyte antigen (HLA) homozygous donor cells (A*33:03-B*44:03-DRB1*13:02) (haplotype frequency: 4.6%) in Koreans were found from the donated cord bloods, ensuring nuclear transfer (NT) cells, if generated therefrom, to be used for about 9% of the total population of South Korea.

Figure 2:
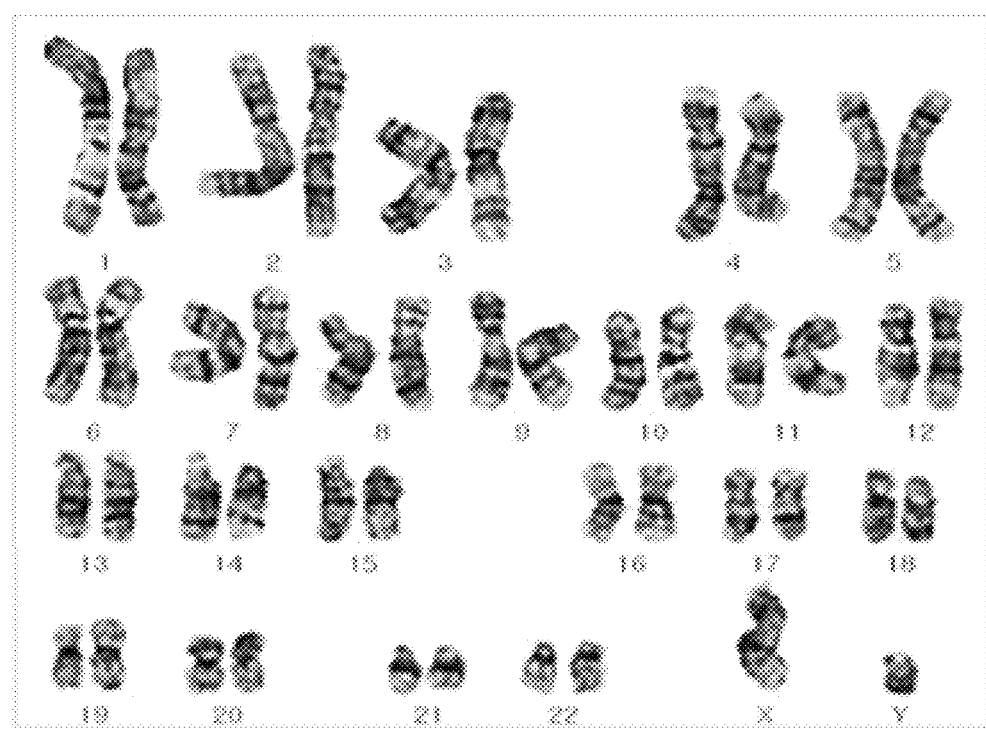
FIG. 2 shows a result of a chromosome test of donor cells in Example 1.

As a result of the screening, hemapoietic stem cells of the HLA A-B-DRB1 haplotypes were selected as donor cells and then cultured in a cell culture flask under the conditions of 5% $CO_2$, and 37° C. The cells were frozen in cryovials together with a Dulbecco's modified Eagle's medium (DMEM) containing 10% of dimethyl sulfoxide (DMSO) and 30% of fetal bovine serum (FBS), as a cryopreservation solution, and stored in a liquid nitrogen tank until use. The cells were subject to a chromosome test (see FIG. 2). The cells were thawed before nuclear transfer (NT) and then cultured in 4-well dishes with confluency, and then synchronized in G0/G1 phase while cultured in 0.5%-FBS DMEM/F-12 media for 2 days.

Example 2

2. 1. Recovery and Generation of Oocytes

This experiment was conducted with the approval of the Stem Cell Research Oversight (SCRO) Committe of the CHA Regenerative Medicine Institute (CHARMI) and the Essex Institutional Review Board (EIRB).

20-32 year old women were recruited through web-based advertising, and their reproductive, medical, and psychological health status were tested according to the American Society for Reproductive Medicine (ASRM) guidelines. The experiment was conducted on the women with BMI<28 $Kg/m^2$ who passed both the medical and psychological tests.

Ovarian stimulation was performed according to established clinical IVF guidelines (Tachibana et al., 2013). After injection of Lupron or hCG into each of the women, the women were sedated with 5-7.5 mg of Midazolam (Versed, Roche, and Nutley. New Jersey, USA) and 50-75 ug of Fentanyl (Abbott Pharmaceutical, Abbott Park, Ill. USA) for about 36 hours, and the oocytes were recovered using a previously described ultrasonography map. Freshly isolated cumulus-oocyte cell complexes (COCs) were collected from an IVF medium (Quinn's IVF medium, SAGE Biopharma, Bedminster, N.J.) and then incubated at about 37° C. in a HTF-Hepes medium (Global Medium) with a 10% serum substitute supplement (SSS; Quinns Advantage Serum, Cooper Surgical). The COCs were treated with hyaluronic acid (100 IU/ml, Sigma, St. Louis, Mo. USA), and the oocytes were sorted according to a degree of maturity to use Midterm II (MII) oocytes for NT.

2.2. Euncleation of Oocytes and Somatic Cell Nuclear Substitution and Activation Enucleation of the oocytes may be performed using a disclosed known method (Tachibana et al., 2013). Enucleation of the oocytes and nuclear substitution of somatic cells were performed using a stage warmer, a narishige micromanipulator, an Oosight™ imaging system (poloscopic microscopy), and a laser-equipped inverted microscope. Optionally, a piezo-equipped inverted microscope may be used instead of the laser-equipped inverted microscope.

The oocytes were placed in a droplet of a HTF-Hepes medium (Global Medium) containing cytochalasin B (5 μg/ml) and caffeine (1.25 mM), and the droplet was covered with an oil for tissue culture and incubated at about 37° C. for about 10 to 15 minutes. Caffeine as a protein phosphatase inhibitor inhibits premature activation to improve growth of cloned embryos and consequently increase blastocyst formation rate. Then, the oocytes were fixed with a holding pipette to position the spindles close to the 2 to 4 o'clock positions, and the zona pellucid adjacent to the spindles was punctured with a laser pulse and an injection pipette was inserted through the opened part to take a small amount of the cytoplasm surrounded by a plasma membrane and the contacted spindles. Optionally, instead of the laser pulse, a piezo pulse may be used to punctuate the zona pellucid (ZP).

Next, the nuclear donor cell was taken with a micropipette and then transferred to a small droplet containing a Sendai virus envelope protein (HJV-E extract, Isihara Sangyo Kaisha). Then, the nuclear donor cell of Example 1 was inserted into the perivitelline space on the opposite side of the first polar body.

After the fusion was confirmed, the generated oocytes were further cultured in a Global 10% SPS medium for about 30 minutes or 2 hours.

Activation was performed in a 0.25 mM d-sorbitol buffer containing 0.1 mM potassium acetate, 0.5 mM magnesium acetate, 0.5 mM HEPES, 1 mg/ml of fatty acid-free BSA by applying electrical pulses (2×50 μs DC pulses, 2.7 kV/cm). The activated cells were cultured in a Global Medium (except for serum) containing 2 mM DMAP under the conditions of 5% $CO_2$ at 37° C. for about 4 hours, and then further cultured in the Global Medium supplemented with 10% FBS, 12 μM BME (β-mercaptoethanol), CARM (2 μg/ml) and 10 nM TSA (Trichostatin A) under the conditions of 5% $CO_2$, 5% $O_2$, and 90% $N_2$ at 37° C. for about 12 hours. Subsequently, after confirmation of pronuclear formation, the cells were further cultured a TSA-free Global Medium supplemented with 10% FBS and 12 μM BME under the conditions of 5% $CO_2$, 5% $O_2$, and 90% $N_2$ at 37° C. up to 7 days. Then, CARM mRNA was injected into the blastomere with a micro injection system at a 4-cell stage. Optionally, HDAC1, SIRT2, or KDM4D may be added instead of CARM.

Example 3

Stem Cell Line Preparation from NT Cells and Characteristic Analysis

The blastocyst cultured in Example 2 was treated with an acidic Tyrode solution (pH 2.0) for several seconds to remove the zona pellucid (ZP). After removal of the ZP, the embryos were vigorously washed in a Hepes-HTF medium to remove even a trace amount of the Tyrode solution. The inner cell mass (ICM) was isolated using a laser-assisted blastocyst excision system (Hamilton-Thorne Inc.) and the remaining part of the blastocyst (the trophoblast) was discarded to confirm that the blastocyst was no longer intact. One day before plating, the ICM was plated onto a prepared MEF, wherein the entire embryo was plated when the cloned blastocyst had an indistinguishable ICM. The hPSC induction medium contained a serum replacement (5% SR, Invitrogen), FBS (10%, Hyclone), plasmamate (5%), bFGF (32 ng/ml), and human LIF (2000 units/ml, Sigma-Aldrich) supplemented with knockout-DMEM. The ICM was cultured in the same medium for 3 days without change, and about ⅓ of the medium was replaced on the $4^{th}$ day. From the $6^{th}$ day, about ½ of the medium was replaced every other day. Initial growth (outgrowth) was confirmed within 7 days after the plating.

Figure 3:
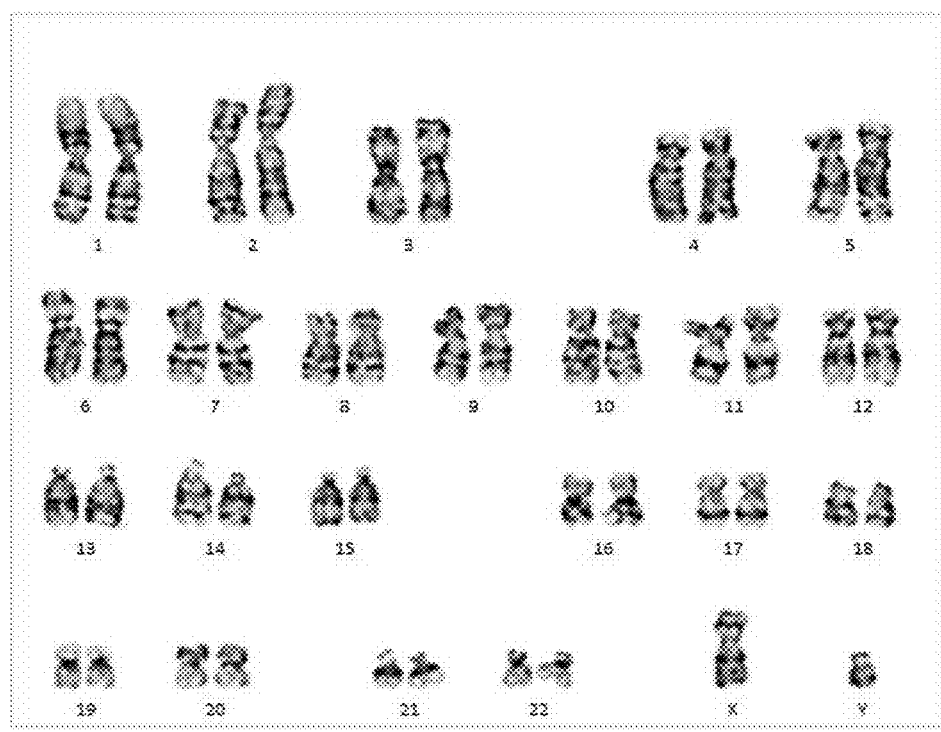
FIG. 3 shows a result of a chromosome test of nuclear transfer (NT) cells generated in Example 3.
Figure 4:
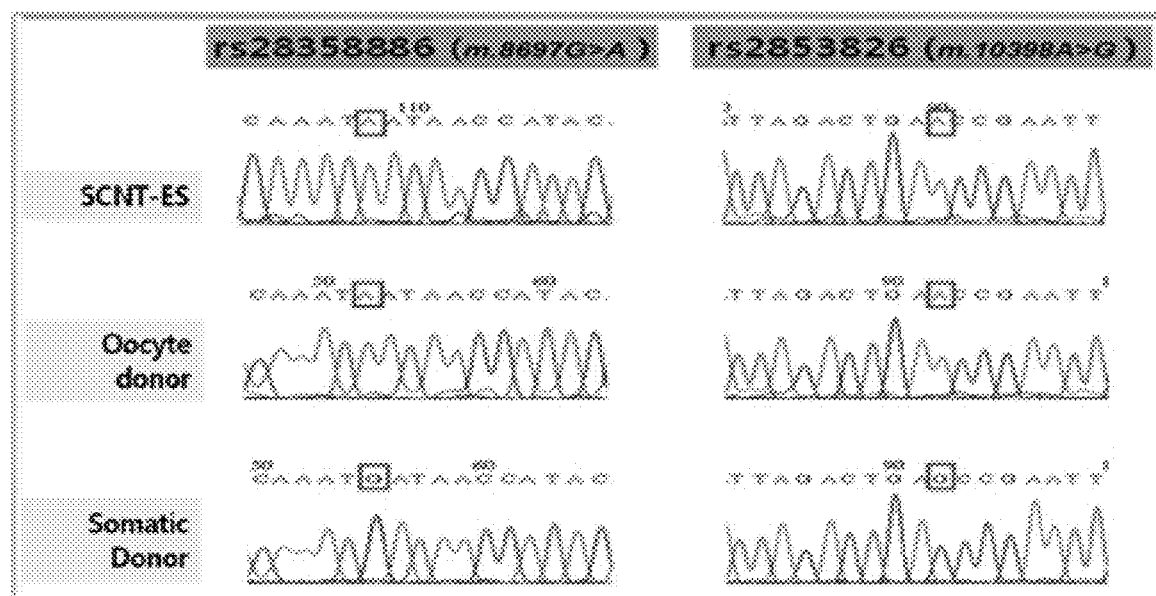
FIG. 4 shows the comparative results of (a) a genomic DNA test and (b) a mitochondrial DNA of the NT cells of Example 3 by comparing donor somatic cells with donor oocytes.
Figure 5:
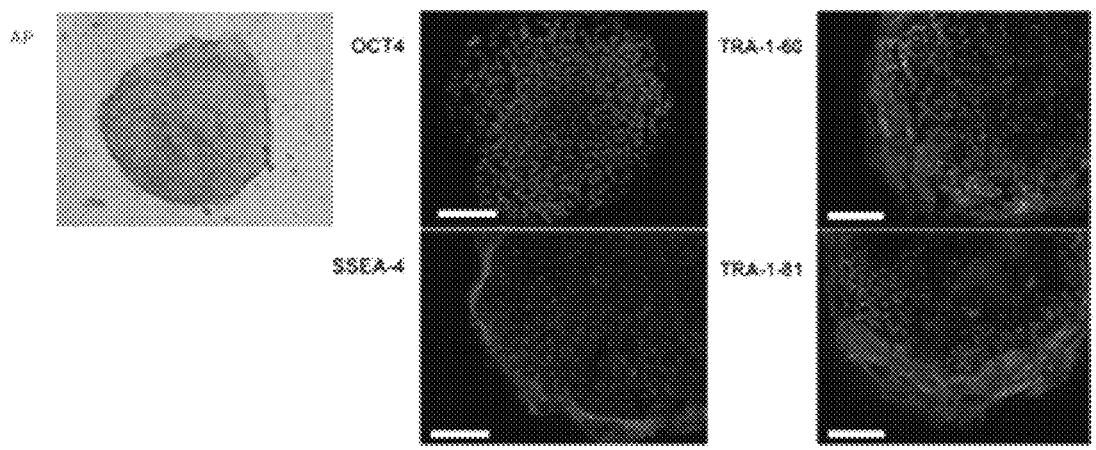
FIG. 5 shows the results of immunochemistry of stem cell markers in the NT cells of Example 3.
Figure 6:
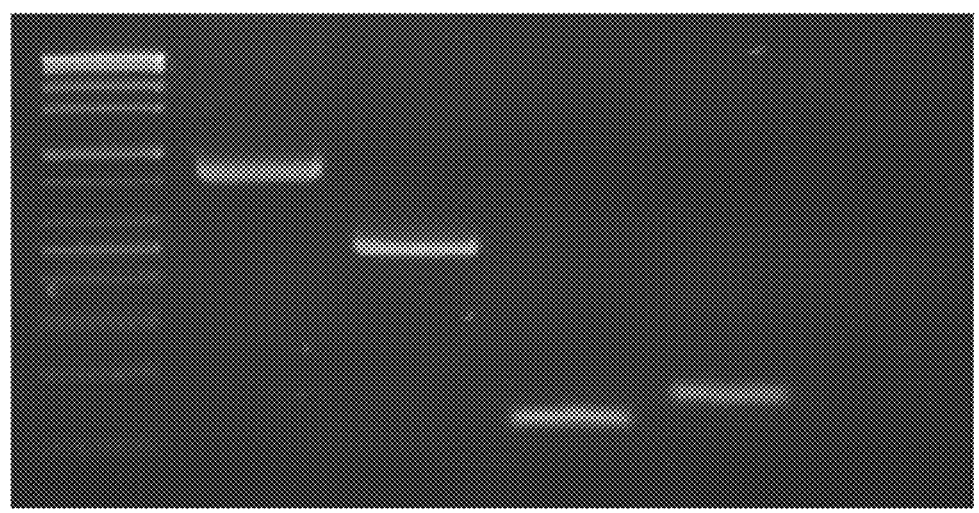
FIG. 6 shows the results of real-time polymerase chain reaction (RT-PCR) of the stem cell markers in the NT cells of Example 3.
Figure 7:
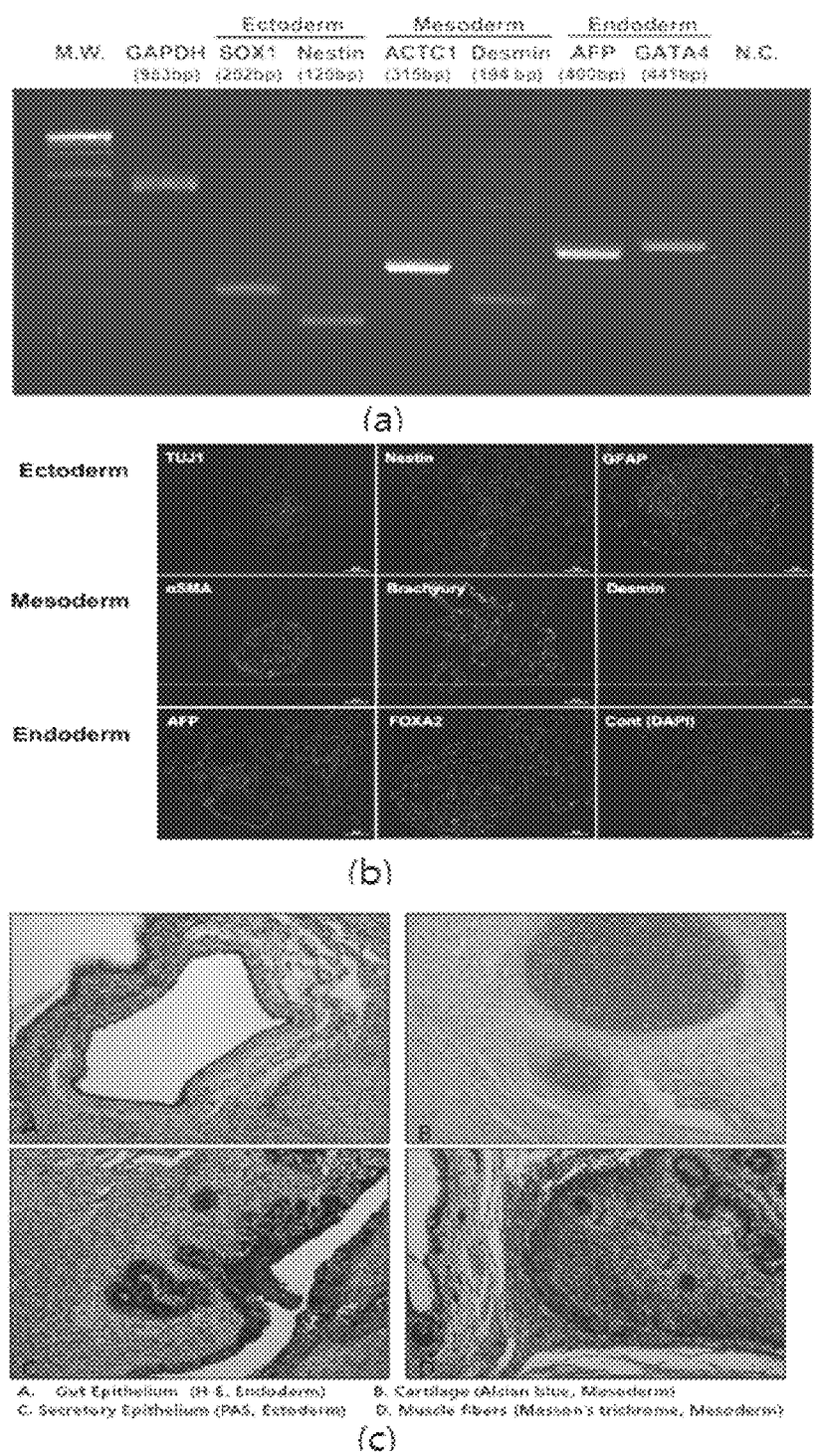
FIG. 7 shows the results of testing the pluripotency of the NT cells of Example 3 to differentiate into 3-germ layer-derived cells, and in particular, (a) results of immunohistochemistry of 3-germ layer differentiation markers after formation of embryoid bodies and incubation for 14 days, (b) RT-PCR results of the markers, and (c) histological analysis results of teratoma after injection into immunodeficient mice.

For further proliferation, colonies having ESC shape were selected and characterized, and cytogenetic analysis was performed. Colonies were expanded and frozen before the $12^{th}$ day. Characteristic analysis of the cells was performed by a chromosome test (G-banding), DNA fingerprinting, and mitochondrial DNA genotyping. The results are shown in FIGS. 3 and 4. To confirm the expression of pluripotent stem cell markers of the cells, the activity of alkaline phosphatase activity was confirmed by AP staining, Oct4, SSEA-4, TRA 1-60 and TRA 1-81 were analyzed by immunocytochemistry, and the expression of Oct4, Nanog and Sox-2 markers was analyzed by RT-PCR. The results are shown in FIGS. 5 and 6. From these results, the derived cells were found to be stem cells. In addition, to confirm the pluripotency to differentiate into 3-germ layer-derived cells, embryoid bodies (EBs) were formed in vitro and cultured, followed by immunochemistry and RT-PCR to identify the expression pattern of the 3-germ layer-derived differentiation marker (see FIGS. 7A and 7B). To confirm pluripotency in vivo, stem cells were injected into the testis or subcutaneous tissue of immunodeficient mice to induce teratoma formation, and the pluripotency was then histologically determined by H-E and special staining. The results are shown in FIG. 7C.

Example 4

Cryopreservation and Banking of NT Cells

The cells prepared in Example 3 were classified according to homozygosity, stored, and recorded in a document or a program. In particular, information on the cell donors was stored together to enable future use directly or in the form of differentiated cells for autologous or allogenic recipients (patients).

Example 5

Differentiation of Functional Retinal Pigment Epithelial Cells (RPE) from NT-Derived Stem Cells To induce differentiation into RPEs, undifferentiated NT-derived stem cells were mechanically divided into several clumps (each containing about 300 to 600 undifferentiated embryos stem cell lines) of NT-ES cells using a sterilized tip under a dissecting microscope. The clump forms of NT-derived stem cells were seeded in low attachment 6-well plates (Corning, Calif., USA) supplemented with 15% (v/v) Knockout™ serum (EBDM; Knockout™ DMEM (Thermo Scientific, (Thermo), 1% (v/v) glutamax (Thermo), 1% (v/v) NEAA (Thermo), 1% (v/v) penicillin-streptomycin) and cultured in a floating state for 4 days. The cultured embryos were transferred and adhered to a culture dish to induce RPE differentiation.

Isolation of Differentiated Retinal Pigment Epithelial Cells from NT-Derived Stem Cells The embryoid body was placed to adhere to a 6-well culture dish with a 0.1% gelatin coating, and subjected to static culture in an incubator for 3 days. Then, while changing the EBDM culture medium every 2 to 3 days, the cells were cultured for about 50 to 55 days until retinal pigment epithelial cells appeared among the cells growing from the embryoid body. To separate RPE cells having a color due to pigmentation, the cells were washed twice with a physiological saline solution (DPBS containing $Ca_2+Mg_2+$(Thermo)) and then cultured in a physiological saline (Type IV collagenase (Thermo) in DPBS with $Ca_2+Mg_2+$ (Thermo)) containing collagenase type 4 in an incubator maintained at about 37° C. under 5% $CO_2$ for about 2 hours. To remove enzymes, cell clusters detached from the culture dish were collected in a 50 ml tube and washed twice with a DMEM-FBS culture solution using a centrifuge (1500 rpm, 5 min). The cell clusters were transferred to a 60-mm Petri dish, and then retinal pigment epithelial cells (pigmented cell clusters) were collected using a thin glass pipette from other cell masses under a dissecting microscope.

Maturation and Proliferation of Differentiated Retinal Pigment Epithelial Cells from NT-Derived Stem Cells The retinal pigment epithelial cell clusters (pigmented cell clusters) were washed twice with a physiological saline solution (DPBS without $Ca_2+Mg_2+$(Thermo)) and then treated with an isolation enzyme solution (1:1 mixture of 0.25% Trypsin-EDTA (Thermo) and Cell Dissociation Buffer (Thermo)) to isolate single cells. The isolated retinal pigment epithelial cells were washed with a DMEM-FBS culture solution using a centrifuge (1500 rpm, 5 min), then suspended in an EGM2 culture solution (Lonza, PA, USA) using a centrifuge (1500 rpm, 5 min), transferred to a 4-well culture dish with 0.1% gelatin coating, and then cultured in the EGM-2 culture solution until each 4-well culture dish was packed with 200,000 cells. After about 3 to 4 days when the culture dish was packed with the cells, the culture medium was replaced with a RPE differentiation culture solution (RGMM, 1:1 mixture of EBDM and DMEM-FBS media) to visualize shapes and characteristics of the retinal pigment epithelial cells, and the cells were further incubated for 7 days.

Figure 8:
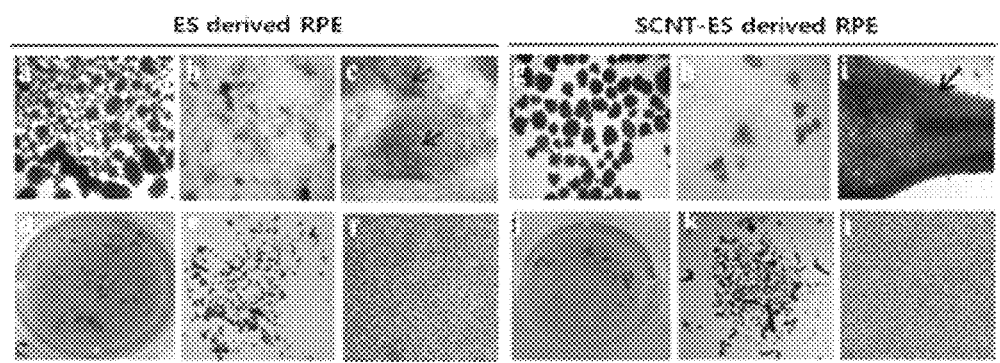
FIG. 8 shows that that there is no difference in shape and differentiation marker between (a) the embryonic stem cell-derived RPE cells and (b) retinal pigment epithelial (RPE) cells obtained from the NT-derived stem cells in Example 3.
Figure 8:
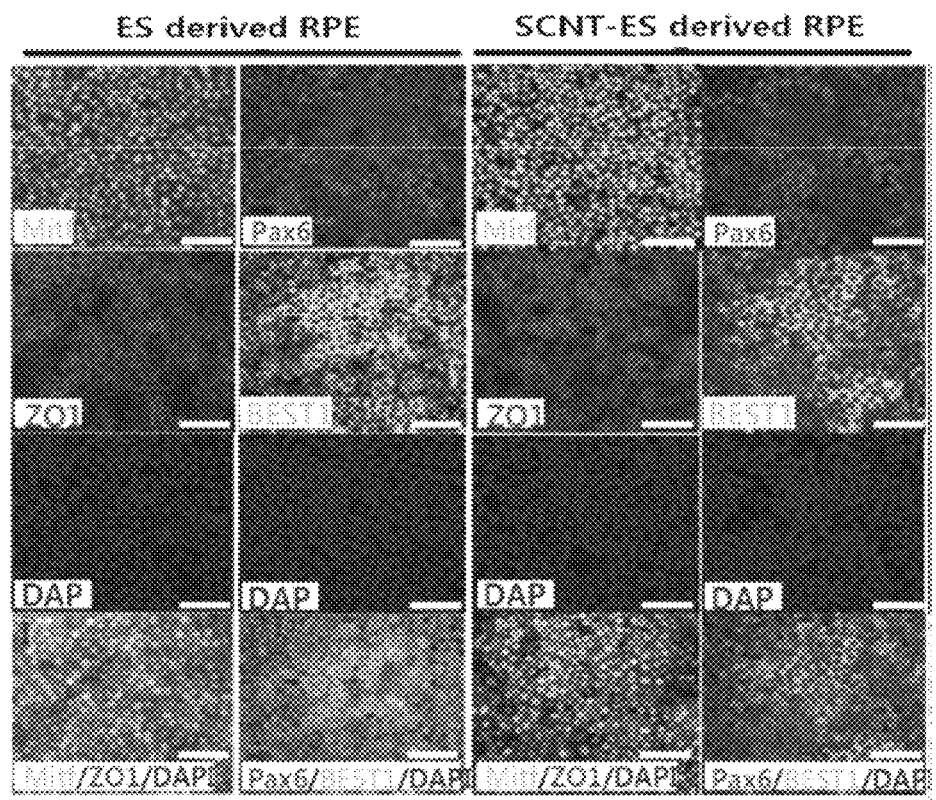

The retinal pigment epithelial cells were sub-cultured using the same isolation enzyme solution as used above, and functional retinal pigment epithelial cells were obtained through proliferation using a EGM2 medium and aging using a RGMM medium. The retinal pigment epithelial cells obtained from the $2^{nd}$ and $3^{rd}$ passages were frozen using a freezing solution (90% v/v FBS (Thermo) and 10% v/v DMSO (Sigma)) at a concentration of 2 million cells per mL of the cryovial and stored until use. Some of the retinal pigment epithelial cells were used for characteristic analysis. FIGS. 8A and 8B show that there is no difference in shape and differentiation marker between the embryonic stem cell-derived RPE cells and the RPE cells obtained from the NT-derived stem cells in Example 3.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

The invention claimed is:

1. A method of generating immunocompatible nuclear transfer (NT) cell-derived stem cells, the method comprising:
 a) obtaining HLA-A, HLA-B and HLA-DRB1 haplotype homozygous somatic cells by:
  a1) screening for human leukocyte antigen HLA-A, HLA-B, and HLA-DRB1 homozygosity in a plurality of donor tissues, and
  a2) isolating HLA-A, HLA-B, and HLA-DRB1 haplotype homozygous cells from the plurality of donor tissues;
 b) generating NT cells by:
  b0) isolating nuclei from the HLA-A, HLA-B, and HLA-DRBl haplotype homozygous somatic cells;

b1) enucleating oocytes, wherein the enucleation is performed in a medium comprising a protein phosphatase inhibitor;

b2) fusing the isolated nuclei of the HLA-A, HLA-B, and HLA-DRBI haplotype homozygous somatic cells to the enucleated oocytes, thereby creating NT cells, wherein the fusing is performed in a medium containing Sendai virus or a Sendai virus extract;

b3) activating the NT cells of b2) by electrical pulses;

b4) providing post-activating NT cells by incubating the NT cells of b3) in a post-activation medium, wherein the post-activation medium comprises 6-dimethylaminopurine (6-DMAP), trichostatin A (TSA) and an epigenetic modifying agent that is involved in modification of a lysine demethylase (KDM) domain protein, and wherein the epigenetic modifying agent contacts the nuclei of at least one of the NT cells of b3); and c) generating the stem cells from the post-activating NT cells by:

c1) generating blastocysts from the post-activating NT cells;

c2) isolating inner cell mass (ICM) cells from the generated blastocysts; and c3) further culturing the isolated ICM cells into the stem cells.

2. A method of storing immunocompatible nuclear transfer (NT) cell-derived stem cells, the method comprising:

a) generating immunocompatible nuclear transfer (NT) cell-derived stem cells by the method of claim 1; and b) cryopreserving the stem cells.

3. A method of generating differentiated cells from immunocompatible NT cell-derived stem cells, the method comprising:

a) generating immunocompatible nuclear transfer (NT) cell-derived stem cells by the method of claim 1; and b) generating the differentiated cells for transplantation from the stem cells.

4. The method of claim 3, further comprising, after the step a), cryopreserving the stem cells and thawing the cryopreserved stem cells.

5. The method of claim 3, wherein, in the step b), the differentiated cells are at least one selected from the group consisting of myocardial cells, liver cells, chondrocytes, epithelial cells, urinary tract cells, adipocytes, kidney cells, vascular cells, retinal cells, and neuronal cells.

* * * * *